(12) United States Patent
Panzner

(10) Patent No.: US 8,957,191 B2
(45) Date of Patent: Feb. 17, 2015

(54) NUCLEIC ACID COMPRISING ZWITTERIONIC NUCLEOTIDES

(75) Inventor: Steffen Panzner, Halle (DE)

(73) Assignee: Steffen Panzner, Halle (DE)

( * ) Notice: Subject to any disclaimer, the term of this patent is extended or adjusted under 35 U.S.C. 154(b) by 333 days.

(21) Appl. No.: 13/003,410

(22) PCT Filed: Jul. 13, 2009

(86) PCT No.: PCT/EP2009/058921
§ 371 (c)(1),
(2), (4) Date: Feb. 10, 2011

(87) PCT Pub. No.: WO2010/004054
PCT Pub. Date: Jan. 14, 2010

(65) Prior Publication Data
US 2011/0137019 A1 Jun. 9, 2011

(30) Foreign Application Priority Data

Jul. 11, 2008 (EP) .................................... 08104731

(51) Int. Cl.
| | | |
|---|---|---|
| C07H 21/02 | (2006.01) | |
| C07H 21/00 | (2006.01) | |
| C07H 19/02 | (2006.01) | |
| A61K 48/00 | (2006.01) | |
| C07H 21/04 | (2006.01) | |
| A61K 47/48 | (2006.01) | |

(52) U.S. Cl.
CPC .......... *C07H 21/04* (2013.01); *A61K 47/48038* (2013.01); *A61K 47/48046* (2013.01); *A61K 47/48061* (2013.01); *A61K 47/48123* (2013.01); *C07H 21/00* (2013.01); *C07H 21/02* (2013.01)
USPC ....... 536/23.1; 536/22.1; 536/25.6; 514/44 R; 514/44 A

(58) Field of Classification Search
USPC ...... 536/23.1, 22.1, 25.6; 514/44, 44 R, 44 A
See application file for complete search history.

(56) References Cited

FOREIGN PATENT DOCUMENTS

WO    WO 91/06556 A1    5/1991
WO    WO 2008/074488 A2    6/2008

OTHER PUBLICATIONS

Griffey, R., et al., "2'O-Aminoprpyl Ribonucleotides: A Switterionic Modification That Enhances the Exonuclease Resistance and Biological Activity of Antisense Oligonucleotides," *J. Med. Chem.*, 1996, vol. 39(26), pp. 5100-5109.
Grøtli, M., et al., "Solid-phase Synthesis of Branched RNA and Branched DNA/RNA Chimeras," *Tetrahedron*, 1997, vol. 53(33), pp. 11317-11346.
Merino, E., et al., "RNA Structure Analysis at Single Nucleotide Resolution by Selective 2'-Hydroxyl Acylation and Primer Extension (SHAPE)," *J. Am. Chem. Soc.*, 2005, vol. 127(12), pp. 4223-4231.
Misra, A., et al., "Synthesis and Fluorescence Studies of Multiple Level Oligonucleotides Containing Dansyl Fluorophore Covalently Attached at a 2'-Temrinus of Cytidine via Carbamate Linkage," *Bioconjugate Chem.*, 2004, vol. 15(3), pp. 638-646.
Ozaki, H., et al., "Post-synthetic functionalization of oligodeoxyribonucleotides at the 2'-position," *Tetrahedron Letters*, 2001, vol. 42(4), pp. 677-680.
Polushin, N., et al., "Synthesis of Functionally Modified Oligonucleotides from Methoxyoxalamido Precursors," *Tetrahedron Letters*, 196, vol. 37(19), pp. 3231-3234, (1996).
Prakash, T., et al., "2'-Modified Oligonucleotides for Antisense Therapeutics," *Current Topics in Medicinal Chemistry*, 2007, vol. 7(7), pp. 641-649.
Prakash, T., et al., "*N,N*'-Bis(2-(Cyano)Ethoxycarbonyl)-2-Methyl-2-Thiopseudourea: A Guanylating Reagent for Synthesis of 2'-*O*-[2-(Guanidinium)Ethyl]-Modified Oligonucleotides," *Nucleosides, Nucleotides, and Nucleic Acids*, 2007, vol. 26(2), pp. 149-159.
Teplova, M., et al., "Structural origins of the exonuclease resistance of a zwitterionic RNA," *PNAS*, 1999, vol. 96(25), pp. 14240-14245.
Tsilevich, T., et al., "Aminoacyl Derivatives of Nucleosides, Nucleotiddes, and Polynucleotides," Institute of Molecular Biology, Academy of Sciences of the USSR, Moscow, pp. 831-835; translated from *Izvestiya Akademif Nauk SSSR, Seriya Khimicheskaya*, 1975, vol. 24(4), pp. 916-921.

Primary Examiner — Shaojia Anna Jiang
Assistant Examiner — Michael C Henry
(74) Attorney, Agent, or Firm — Novak Druce Connolly Bove + Quigg LLP; Thomas M. Saunders

(57) ABSTRACT

This invention provides pH-responsive zwitterionic nucleotides and nucleic acids comprising said nucleotides, wherein said zwitterions are constituted from one or more anionic internucleoside linkages and one or more cationic moieties and said zwitterionic nucleotides further comprise either one or more hydrophobic moieties or one or more TEE's with the general structure (I) Hydrophobic element-pH-responsive hydrophilic elements (I).

9 Claims, 1 Drawing Sheet

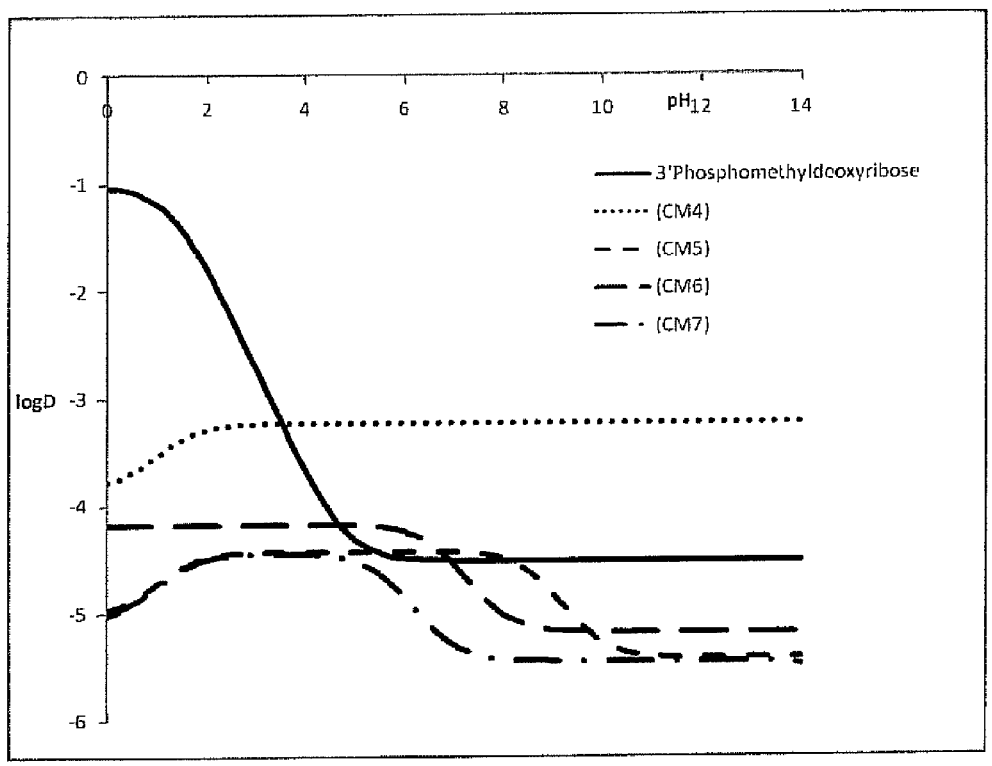

NUCLEIC ACID COMPRISING ZWITTERIONIC NUCLEOTIDES

CROSS-REFERENCE TO RELATED APPLICATIONS

This application is a national phase of International Application No. PCT/EP2009/058921, filed on Jul. 13, 2009, which claims priority to European Patent Application No. 08104731.8, filed on Jul. 11, 2008. The contents of all of these applications are expressly incorporated herein by reference in their entireties.

FIELD OF THE INVENTION

This disclosure describes novel structural elements that enable transport of nucleic acids across biological membranes, in particular cell membranes. The elements are pH sensitive in terms of charge and hydrophilicity and undergo a polar-apolar transition when exposed to low pH.

BACKGROUND OF THE INVENTION

The field of this invention is the transport of nucleic acids and more specifically the transport of oligonucleotides across biological membranes. Penetration of such molecules is hampered by their very hydrophilic and charged nature and efforts have been made to reduce the hydrophilic nature of such molecules by various means. Chemical modification of the internucleoside linkage can eliminate the charged character of the phosphodiester bond, e.g. by using methylphosphonates (Miller and Ts'o 1981, Annu Rep Med Chem 23:295) or can reduce it through incorporation of phosphorothioate bonds (Eckstein 1989, Trends Biochem Sci 14:97) or phosphorodithioate bonds (Nielsen 1988, Tetrahedron Lett 29:2911). Rudolph et al. (1996 in Nucleosides and Nucleotides 15:1725) introduced phosphonoacetate derivatives of oligonucleotides and Dellinger in U.S. Pat. No. 6,693,187 and its continuations U.S. Pat. No. 7,067,641; US2004/0116687 and US2006/0293511 present further data on the synthesis of such compounds. Phosphonoacetates were profiled as derivatives of oligonucleotides with reduced internucleoside charge that are highly nuclease resistant and, when designed as single stranded oligodeoxynucleotides, facilitate catalytic action of RNAseH upon binding to a complementary strand of RNA (in Sheehan et al, Nucl Acid Res 2003, 31:4109-4118). The thymidine dimers presented there display a decreased hydrophilicity at low pH; however, the cellular uptake of an oligonucleotide remained unchanged. In fact, cellular penetration was only achieved after elimination of the carboxylate charge group by esterification with methyl- or butyl groups.

In still other cases, lipophilic conjugation has been used to improve the cellular uptake of oligonucleotides such as single stranded oligodeoxynucleotides or double stranded siRNA molecules (Letsinger et al. in U.S. Pat. No. 4,958,013 or Proc. Natl. Acad. Sci., 86, 6553-6556, 1989 or by Manoharan et al. in U.S. Pat. No. 6,153,737 and U.S. Pat. No. 6,753,423 in combination with single stranded oligonucleotides; Soutschek et al. (2004) Nature, 432(7014), 173-178 or Wolfrum et al. (2007) in Nat Biotech 25:1149-1157 for the delivery of siRNA.

Very recently, Panzner in PCT/EP2007/011188 described nucleosides, nucleotides and nucleic acids derived thereof that are designed for improved cellular uptake and comprise one or more transfection enhancer elements, TEE's. The content of this PCT/EP2007/011188 is included herein by reference.

In brief, pH-responsive transfection enhancer elements (TEE's) have the general structure (I)

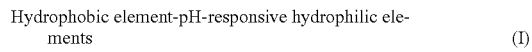

Hydrophobic element-pH-responsive hydrophilic elements (I)

The position of the hydrophilic element within the TEE structure may vary and PCT/EP2007/011188 teaches that the hydrophilic element can be located distal from the link between molecule and TEE. PCT/EP2007/011188 also mentions that the hydrophilic element can be located central within the TEE.

PCT/EP2007/011188 describes the pH-responsive hydrophilic element as weak acids having a pKa of between 2 and 6, preferred of between 3 and 5. Said weak acids may be selected from carboxyl groups, barbituric acid and derivatives thereof, xanthine and derivatives thereof, wherein in some embodiments the xanthine derivatives are pyrimidines.

PCT/EP2007/011188 also describes the pH-responsive hydrophilic element as zwitterionic structures comprising a combination of weak or strong acidic groups with weak bases, the latter having a pka of between 3 and 8, preferred of between 4.5 and 7.

PCT/EP2007/011188 further gives guidance how to achieve the specific pKa's of said hydrophilic elements, inter alia by substitution hydroxymethyl-, hydroxyethyl-, methoxymethyl-, methoxyethyl-, ethoxymethyl-, ethoxyethyl-, thiomethyl-, thioethyl-, methylthiomethyl-, methylthioethyl-, ethylthiomethyl-, ethylthioethyl-, chlorid-, chlormethyl-vinyl-, phenyl-, benzyl-, methyl-, ethyl-, propyl-, isopropyl- and tert-butyl or cyclohexyl groups.

The hydrophobic element of the TEE of PCT/EP2007/011188 can be linear, branched or cyclic chains with a minimum chain length of 6 units, sometimes as short as 4 units. The hydrophobic element often comprises more than 6 and up to 40 units, often between 6 and 20 units, wherein said units of said hydrophobic element often are carbon atoms, hydrocarbons or methylene groups.

PCT/EP2007/011188 also teaches that branching of the main chain of said hydrophobic element is possible and such branches may comprise building blocks, such as methyl-, ethyl-, propyl-, isopropyl-, methoxy-, ethoxy-, methoxymethyl-, ethoxymethyl-, methoxyethyl-, ethoxyethyl- and vinyl- or halogen groups or mixtures thereof.

In some embodiments of PCT/EP2007/011188 the hydrophobic element may derive from sterols, said sterols may be further substituted.

PCT/EP2007/011188 also mentions the insertion of one or more heteroatoms or chemical groups into the hydrophobic element of the pH-responsive transfection enhancer elements (TEE's). Such heteroatoms or chemical groups may be selected from —O—, —S—, —N(H)C(O)—, —C(O)O—, —OC(O)N(H)—, —C(O)—, —C(O)—N(H)—, —N(H)—C(O)—O—, —CH=N—, —O—C(O)—, —N=CH— and/or —S—S—, amino acids or derivatives thereof, α-hydroxy-acids or β-hydroxy acids.

One central disclosure of PCT/EP2007/011188 is the hydrophilic-hydrophobic transition of TEE's in response to an acidification of the environment and application of such knowledge towards the design of nucleosides and nucleotides and detailed information on the design of modified nucleosides, nucleotides, internucleoside linkages or nucleic acids with enhanced membrane permeability is given therein.

As further described in the PCT/EP/2007/011188, the nucleobases contribute to the log D of a nucleic acid; their average log D at pH 7.4 is about −1.3 for DNA and −1.4 for RNA; the respective values at pH4 are −1.7 and −1.8 for DNA or RNA. The nucleobases therefore contribute a pH-dependent value of log D to the entire structure.

PCT/EP2007/011188 is also disclosing contributions of an average unit of the backbone, said contributions are −2.5 and −3 per abasic nucleotide in phosphodiester DNA and RNA, respectively, and −2.0 and −2.4 for the phosphorothioate building blocks.

The table 1 below integrates these values and provides a survey for the log D values of abasic polynucleotides and nucleic acids with average base use. The "monomer increment" describes the log D contribution for each additional nucleotide in a nucleic acid structure, the offset is the extrapolated log D for 0 nucleotides and the log D of larger structures is calculated as log D(n-mer)=offset+n*monomer increment, wherein n represents the number of monomer units in a nucleic acid.

Table 1: log D values for nucleic acid structures. The table shows calculated log D values for monomers to tetramers of abasic nucleic acids and the resulting monomer increment and offset values from these values. For the calculation of log D values of statistical 20 mer oligonucleotides, the contribution of average nucleobases was also taken into account.

|  |  | abasic oligomers # of monomers | | | | monomer increment | offset | oligomer with nucleobases 20 |
| --- | --- | --- | --- | --- | --- | --- | --- | --- |
|  |  | 1 | 2 | 3 | 4 |  |  |  |
| deoxy | pH 7.4 | −5.6 | −8.1 | −10.6 | −13.2 | −2.5 | −3.0 | −79.2 |
|  | pH 4 | −4.6 | −7.9 | −10.5 | −13.0 | −2.5 | −2.9 | −86.8 |
| 2' OH | pH 7.4 | −5.8 | −8.9 | −11.9 | −15.0 | −3.0 | −2.8 | −83.2 |
|  | pH 4 | −5.0 | −8.8 | −11.9 | −14.9 | −3.0 | −2.8 | −90.8 |
| PTO/DNA | pH 7.4 | −5.3 | −7.2 | −9.1 | −11.1 | −1.9 | −3.3 | −74.3 |
|  | pH 4 | −3.6 | −6.9 | −9.1 | −11.1 | −2.0 | −3.0 | −82.6 |
| PTO/RNA | pH 7.4 | −5.2 | −7.7 | −10.1 | −12.5 | −2.4 | −2.8 | −78.4 |
|  | pH 4 | −4.4 | −7.6 | −10.1 | −12.5 | −2.4 | −2.8 | −86.0 |

According to these calculations, oligonucleotides and longer nucleic acids are highly polar structures with log D values between −75 and −90 for average 20mers.

Also, the nucleic acids become even more polar at lower values of pH; this is a contribution of the nucleobases, not the backbone.

OBJECTS OF THE INVENTION

Cellular uptake, that is penetration of nucleic acids across biological membranes, remains challenging and alternative approaches for this problem still represent a major technical need for this class of substances.

It is therefore an object of this invention to provide novel nucleic acids or their designs with improved cellular penetration.

It is a specific object of the invention to further improve the hydrophilic-hydrophobic transition of nucleic acids in response to external pH stimuli.

BRIEF DESCRIPTION OF THE INVENTION

The present invention provides pH-responsive zwitterionic nucleotides and nucleic acids comprising said nucleotides according to the claims. Further advantageous embodiments of the invention are described in the dependent claims.

This invention provides pH-responsive zwitterionic nucleotides, wherein said zwitterions are constituted from one or more anionic internucleoside linkages and one or more cationic moieties and said zwitterionic nucleotides further comprise either one or more hydrophobic moieties or one or more TEE's.

The ion-pair forming cationic moieties and the internucleoside linkages are in close spatial proximity. In many embodiments of this feature, the cationic moieties are substituted to the 2', 4' or 1' position, preferably to the 2' position of the sugar ring of the nucleotides and form zwitterionic structures with the internucleoside linkage that is connected to the 3' position of said nucleotide. In other aspects, said cationic moieties may form zwitterionic structures with the internucleoside linkage that is connected to the 5' position of said nucleotide.

Structures within this definition are called Ion-Paired Nucleotides, IPNs, throughout this disclosure.

The formation of the zwitterion is dependent on the charged state of both participating ions. Phosphate-based internucleoside linkages such as phosphodiesters or phosphothioates have a pK of about 1 to 1.5 and are fully charged at all pH values greater than 2.5. Zwitterion formation is therefore guided by the availability of the charged cation and is thus dictated by the pK of the CM. A high value of pK results in constant zwitterion formation, a moderate or low value of pK makes this zwitterion formation a function of the pH of the medium. Zwitterion formation between the CM and an internucleoside linkage is a first major contribution to minimize the log D of a nucleic acid. An additional reduction of log D can be achieved through use of TEE's, which also provide a hydrophilic-hydrophobic transition in response to the pH of the medium.

Now, in a first aspect of the invention, pH-responsive nucleotides are provided that comprise one or more zwitterionic structures and one or more TEE's, said zwitterions are constituted from the anionic internucleoside linkage and a cationic moiety, said cationic moiety having a pK equal or greater than 7.5.

In a second aspect of the invention, pH-responsive nucleotides are provided that comprise one or more pH responsive zwitterionic structures, said zwitterions are formed between the anionic internucleoside linkage and a cationic moiety, said cationic moiety having a pK equal or lower than 7.5. In some embodiments of that aspect, additional hydrophobic elements are present.

In a third aspect of the invention, pH responsive nucleotides are provided that comprise one or more pH responsive zwitterionic structures and one or more TEE's, said zwitterions are constituted from the anionic internucleoside linkage and a cationic moiety, said cationic moiety having a pK equal or smaller than 7.5.

The pH in physiological environments may vary and the structures of this invention can be designed to react to such variability. In many aspects, such variation will take place within the interval of pH7.4, which is the physiological pH in the circulation and in many body fluids, and a pH of about 4 to 5, which is reached upon endocytic uptake of outside materials, in some tumor areas or at places of ongoing inflammation. A low pH is also found in the urine and in the intestine as well as in the stomach. In preferred embodiments, the pH-sensitive zwitterionic nucleotides of this invention undergo a hydrophilic-hydrophobic transition between pH7.4 and pH4.

Explicit reference is made to PCT/EP2007/011188 for the definition of TEE's, their hydrophilic and hydrophobic elements and their architecture and their response to the pH of the medium.

In the second aspect of this invention, such TEE may be absent and the pH responsive character of the IPN is mainly contributed from the cationic moieties. In this case, one or more hydrophobic moieties may be present, said hydrophobic elements share the design parameters and the architecture described for TEE's, essentially they are the hydrophobic moieties of a TEE, but the weak acid of the TEE is absent in this aspect of the invention.

In many aspects of the invention the anionic internucleoside is selected from the group of phosphate diesters, phosphothioates or phosphodithioates. It is of course possible to use different internucleoside linkages in a nucleic acid and it is further possible to introduce other substitutions at the internucleoside linkage as long as the internucleoside linkage remains negatively charged.

In some embodiments of this invention, the cationic moieties are connected to the 2' position of a nucleoside. In other embodiments the cationic moieties are connected to the 4' position of a nucleoside. In yet other embodiments, the cationic moieties are connected to the 1' position of a nucleoside, replacing the former nucleobases at C1.

In particular aspects of this invention, the TEE or the hydrophobic moieties are directly linked to a cationic moiety which in turn provides a linkage to a nucleotide.

In other aspects of this invention the TEE's or the hydrophobic moieties on the one hand and the cationic moieties on the other hand may have individual grafting positions at C1, C2 or C4 of the nucleosides.

In preferred aspects of the present invention the hydrophilic-hydrophobic transition of the TEE occurs between pH4 and pH7.5 and the TEE has a guiding pK of between 3 and 6.5. It is known from the reference PCT/EP2007/011188 that the TEE may comprise weak acids or zwitterions, the guiding pK mentioned here is the one which determines the hydrophilic-hydrophobic transition in either case.

Some TEE's may be alkylcarboxylic acids. Other TEE's may comprise a sterol and still others may comprise the carboxylic acid of a sterol.

An important element of this invention is the construction and design of nucleic acids comprising one or more IPN's. The nucleic acids of the present invention are oligonucleotides or polynucleotides and in some embodiments no more than ⅔ of all nucleotides of said nucleic acid are of IPN type.

In other embodiments only nucleotides at one or both flanks of an oligonucleotide or polynucleotide are of IPN type.

In further aspects, the present invention comprehends pharmaceutical compositions comprising nucleic acids further modified with one or more IPN's and pharmaceutically acceptable vehicles therefore.

In still other aspects, the present invention comprehends the use of a pharmaceutical composition according to the present invention for the treatment or prophylaxis of inflammatory, immune or autoimmune disorders, cancers or metabolic diseases of humans or non-human animals.

In another aspect, the present invention comprehends the use of nucleic acids further modified with one or more IPN's for the in vivo, in vitro or ex vivo transfection.

DEFINITIONS

For clarity, the following definitions and understandings are used for important terms of the invention:

IPN1
... means Ion-Paired Nucleotides according to the first aspect of this invention.

IPN2
... means ion-Paired Nucleotides according to the second aspect of this invention.

IPN3
... means Ion-Paired Nucleotides according to the third aspect of this invention.

Log P
... is the ratio of the respective concentrations of a compound in the 1-octanol and water partitions of a two-phase system at equilibrium. The octanol-water partition coefficient (log P) is used to describe the lipophilic or hydrophobic properties of a compound.

Log D
... is the ratio of the equilibrium concentrations of all species (unionized and ionized) of a molecule in 1-octanol to same species in the water phase.

The partition coefficient for dissociative mixtures, log D, is defined as follows:

$$\log D = \log(\Sigma(c_i^{H2O})/\Sigma(c_i^{org})), \text{ where}$$

$c_i^{H2O}$ is the concentration of the i-th microspecies in water and $c_i^{org}$ is the concentration of the i-th microspecies in the organic phase.

Log D differs from log P in that ionized species are considered as well as the neutral form of the molecule. Log D is therefore the log P at a given pH of the medium.

Log P and log D values can be determined experimentally by measuring the partition of a molecule or its ionized forms in octanol/water systems. Experimental values have been generated for a vast amount of individual compounds and expert systems allow extrapolating log P and log D values for novel species. One such expert system is ACD/Labs with the modules ACD/Log P or ACD/log D and ACD/Labs 7.06 has been used for calculations within this disclosure.

Nucleic Acids
... as used herein are the polynucleotides or oligonucleotides defined below, including, without limitation, DNA or RNA.

Polynucleotide
... as used herein refers to any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions.

Oligonucleotides

... as used herein are defined as molecules with two or more deoxyribonucleotides or ribonucleotides, often more than three, and usually more than ten. The exact size of an oligonucleotide may depend on many factors, including the ultimate function or use of the oligonucleotide. Oligonucleotides can be prepared by any suitable method, including, for example, cloning and restriction of appropriate sequences and direct chemical synthesis by a method such as the phosphotriester method of Narang et al., Meth. Enzymol., 68, 90-99, 1979; the phosphodiester method of Brown et al., Method Enzymol., 68, 109-151, 1979 the diethylphosphoramidite method of Beaucage et al., Tetrahedron Lett., 22, 1859-1862, 1981 the triester method of Matteucci et al., J. Am. Chem. Soc., 103, 3185-3191, 1981 or automated synthesis methods; and the solid support method of U.S. Pat. No. 4,458,066.

Transfection

... is used widely to specifically describe the disappearance of a concentration gradient across a biological membrane in vivo, in vitro or ex-vivo. It comprises transport across, or diffusion through, penetration or permeation of biological membranes irrespective of the actual mechanism by which said processes occur. The agents to be transfected may comprise nucleic acids, polynucleotides or oligonucleotides.

REF1

... means the PCT/EP2007/011188, all content of which is included herein by reference.

Cationic Moieties (CM's)

The cationic moiety of this invention is a nitrogen base and can be a primary, secondary, tertiary or quarternized nitrogen. The chemical structures comprising the CM can be linear, cyclic or branched and the structures may have saturated bonds. The CM may also comprise unsaturated bonds or it may be of aromatic character. The CM may thus be selected from the group comprising alkylamines, alkenylamines, alkylammonium salts or alkenylammonium salts, cyclic amines, their quarternized homologues and the like.

The CM may also comprise more than one nitrogen atom and may thus be selected from the group comprising guanidinium salts, imidazols, pyrazols, imidazolines, imidazolidines, pyrazolines, pyrazolidines, pyrazines, piperazins, pyrimidines, pyridazins, hydrazines and the like.

The CM may also comprise further heteroatoms and in some embodiments such heteroatoms are oxygen or sulphur atoms. Morpholino groups are a specific representative of a CM comprising heteroatoms. Amongst the oxygen-substituted amines, moieties that are substituted in β-, γ- or δ-position of the nitrogen atom are used with preference. CM's may therefore comprise nitrogen bases having one or more of hydroxyethyl-, hydroxypropyl-, hydroxyisopropyl or hydroxybutyl groups. Of course, these CM's may also comprise other substituents such as lower alkyl groups comprising between 1 and 6 C-atoms and mixed substitutions are possible within the valency of the nitrogen atom.

The CM's may also comprise acetal, hemiacetal, ester, ether, thioether, amide or urethane functions. Preferred CM's comprise such functions in β-, γ- or δ-position. Specific CM's comprise the acetals, hemiacetals, esters, ethers, thioethers, ketones, amides or urethanes of serine, homoserine, threonine, homothreonine or 2-amino-5-hydroxycarboxylic acid.

The cationic moieties may further be selected from the compounds listed in the table 2 below and substituted forms thereof. Said substitutions can comprise lower alkyl groups having between 1 and 6 carbon atoms, halogen atoms or hydroxyl or thiol groups.

TABLE 2

List of some CM of the invention.

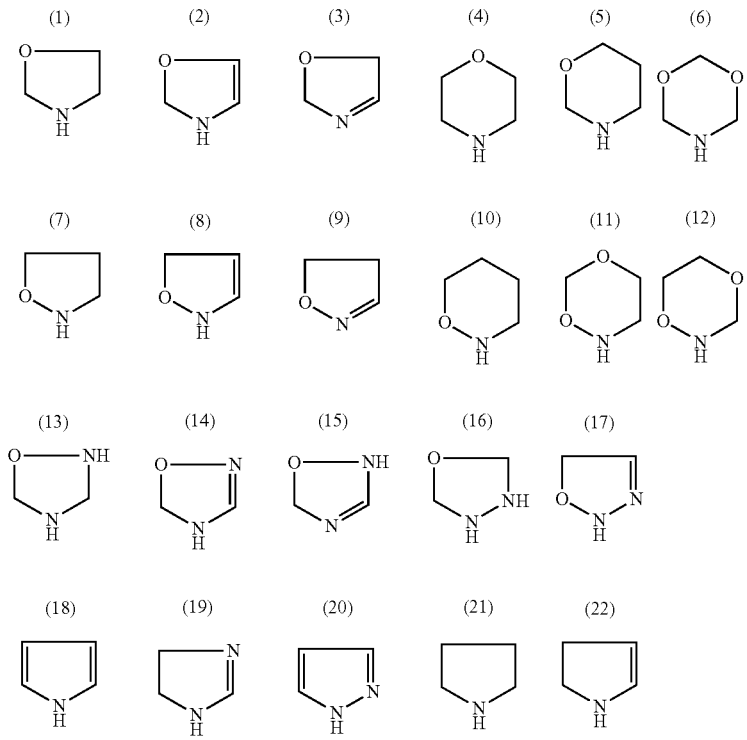

TABLE 2-continued
List of some CM of the invention.

TABLE 2-continued
List of some CM of the invention.
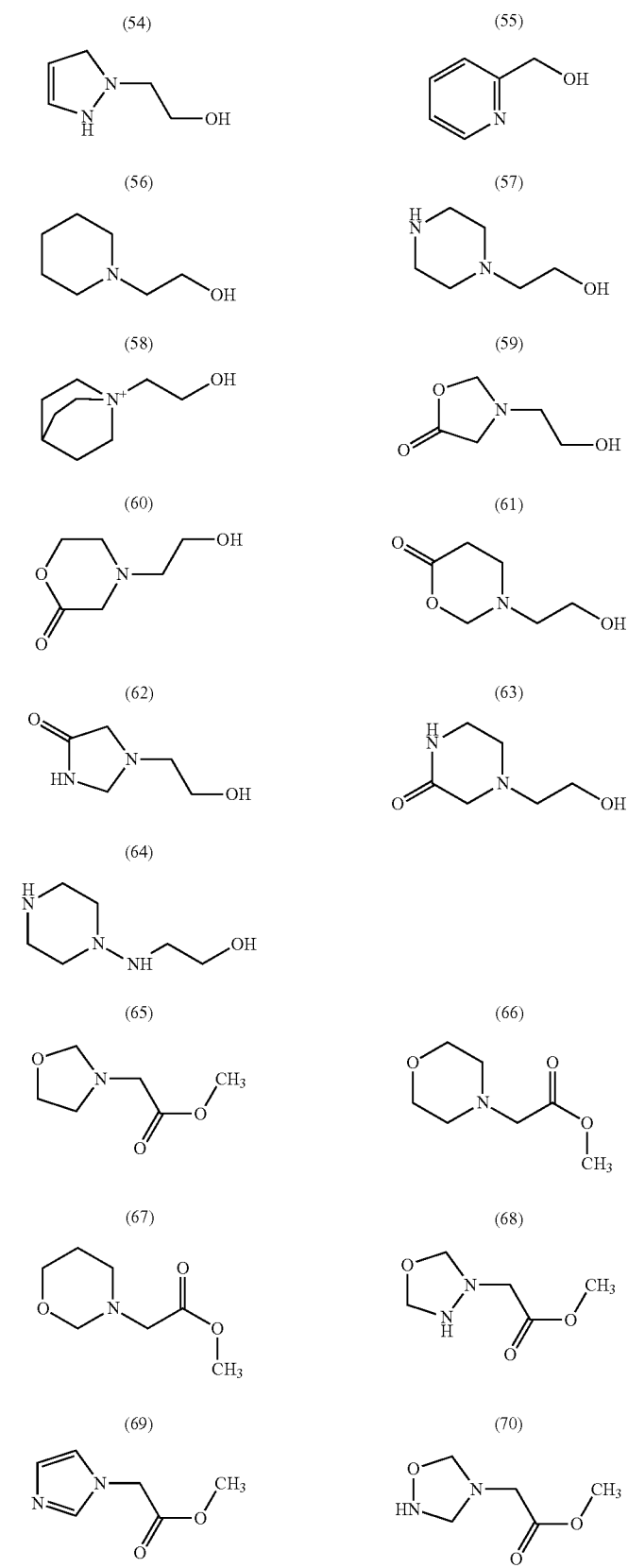

TABLE 2-continued
List of some CM of the invention.
(71)
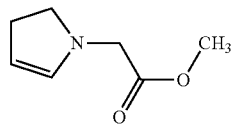
(72)
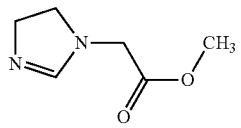
(73)
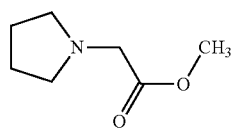
(74)
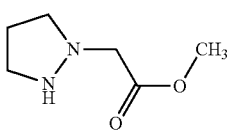
(75)
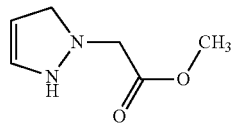
(76)
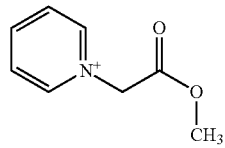
(77)
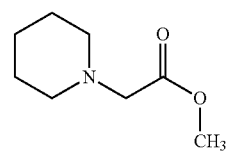
(78)
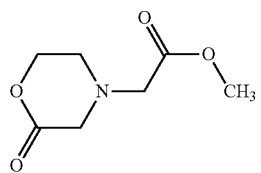
(79)
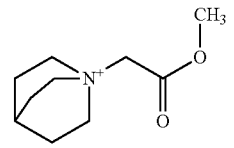
(80)
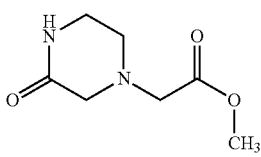
(81)
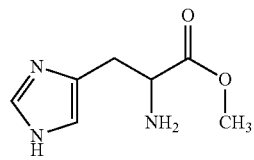
(82)
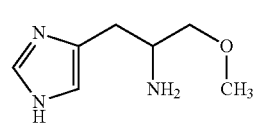
(N1)
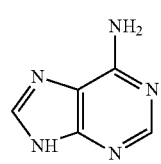
(N2)
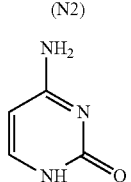

TABLE 2-continued
List of some CM of the invention.
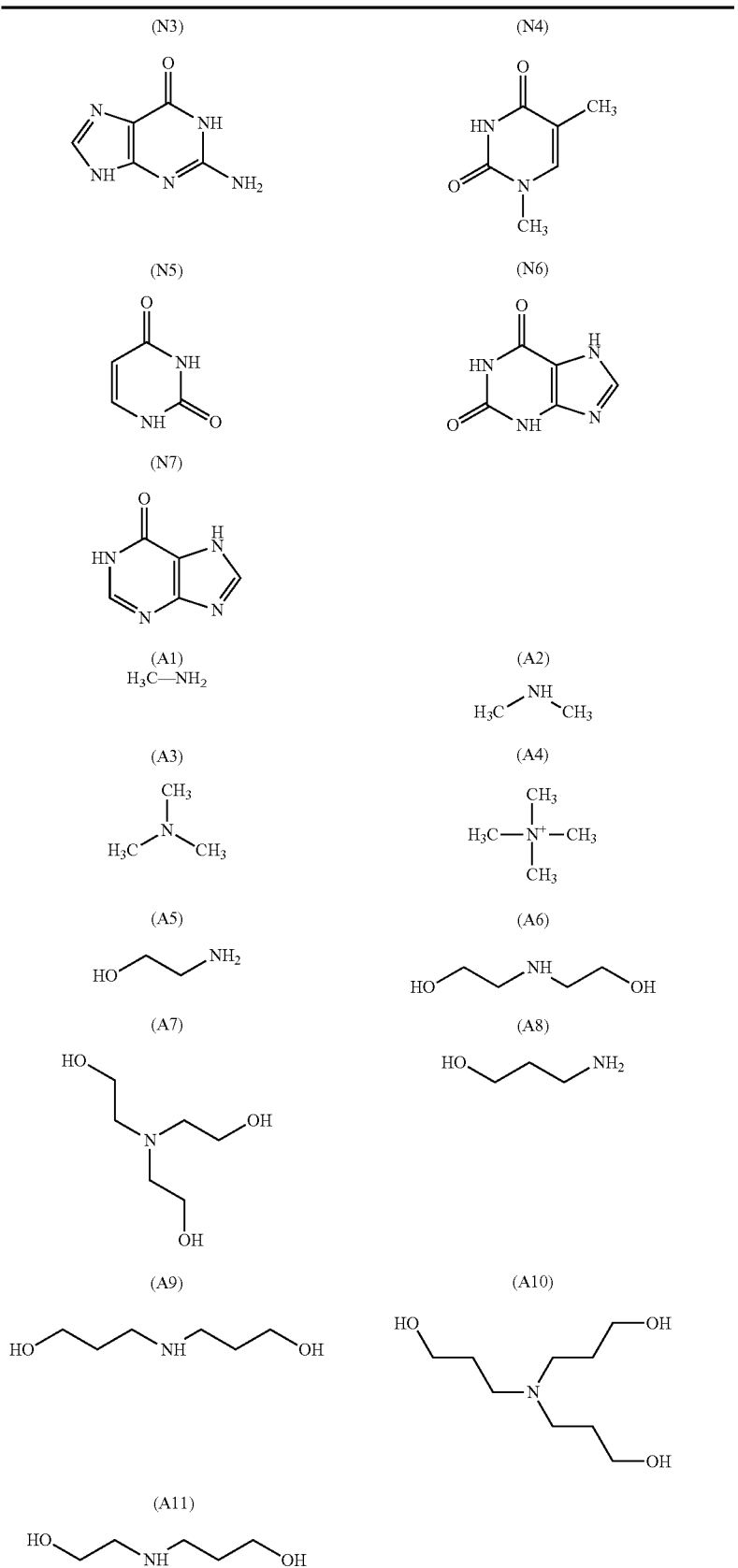

TABLE 2-continued
List of some CM of the invention.
(A12)
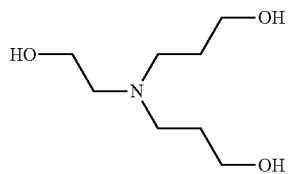
(A13)
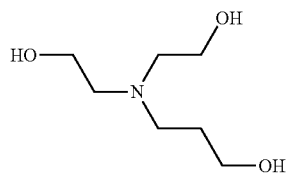
(AE1)
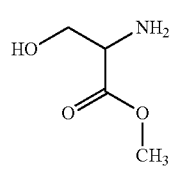
(AE2)
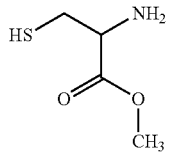
(AE3)
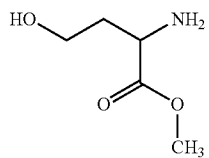
(AE4)
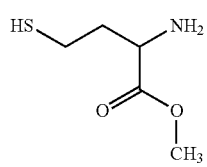
(AE5)
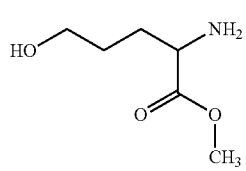
(AE6)
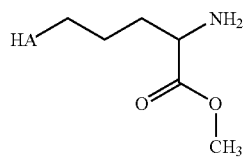
(AE7)
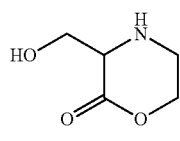
(AE8)
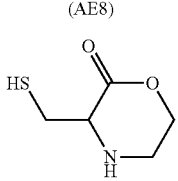
(AE9)
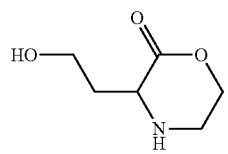
(AE10)
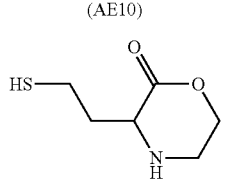
(AE11)
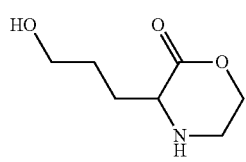
(AE12)
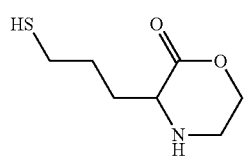

TABLE 2-continued
List of some CM of the invention.
(AE13)
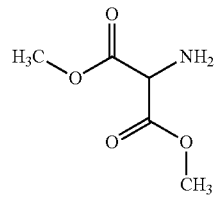
(AE14)
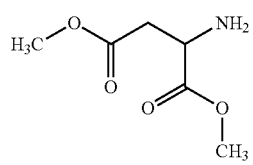
(AE15)
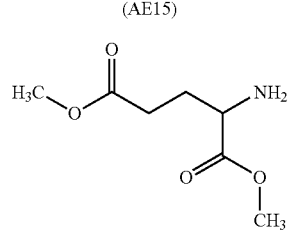
(AE16)
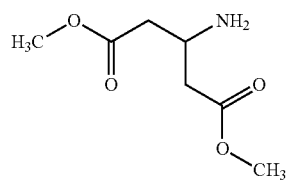
(AE17)
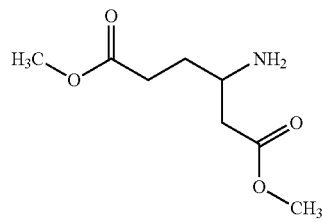
(AE18)
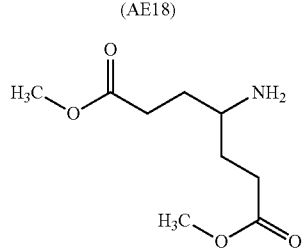
(AE21)
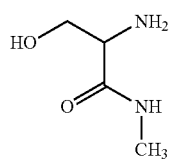
(AE22)
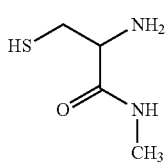
(AE23)
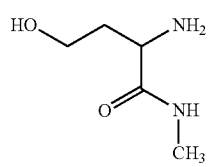
(AE24)
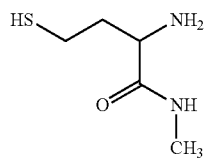
(AE25)
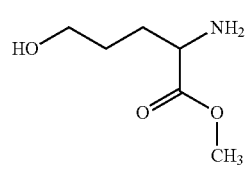
(AE26)
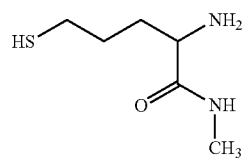

TABLE 2-continued
List of some CM of the invention.
(AE27)
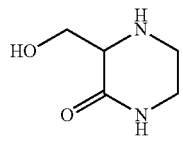
(AE28)
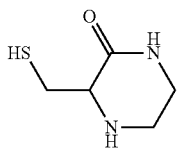
(AE29)
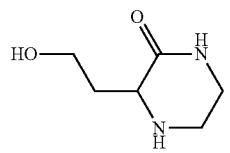
(AE30)
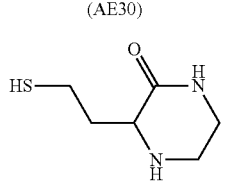
(AE31)
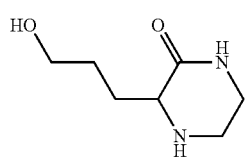
(AE32)
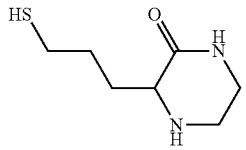
(AE33)
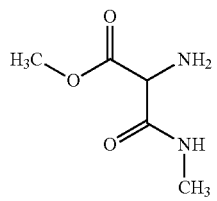
(AE34)
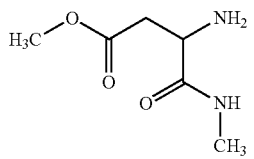
(AE35)
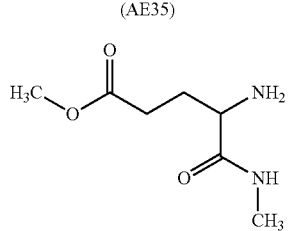
(AE36)
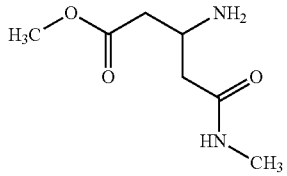
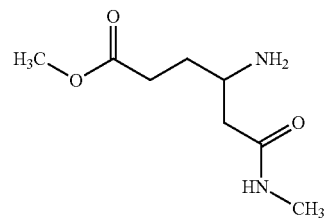
(AE37)
(AE38)
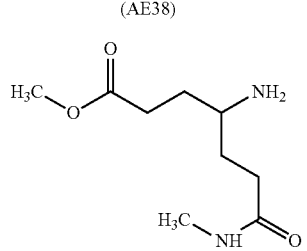

TABLE 2-continued

List of some CM of the invention.

(AE39) (AE40) (AE41) (AE42) (AE43) (AE44) (AE45) (AE46) (AE47) (AE48) (AE49) (AE50) (AE51) (AE52)

TABLE 2-continued
List of some CM of the invention.
(AE53)
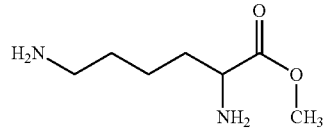
(AE54)
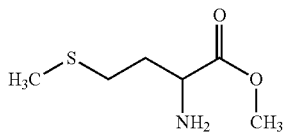
(AE55)
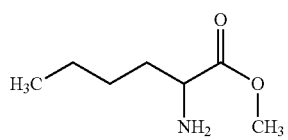
(AE56)
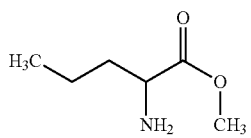
(AE57)
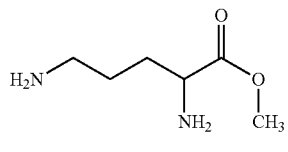
(AE58)
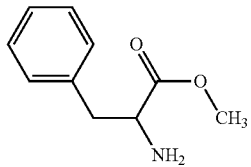
(AE59)
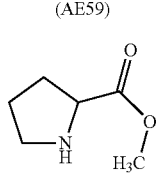
(AE60)
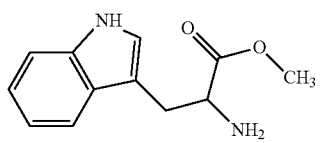
(AE61)
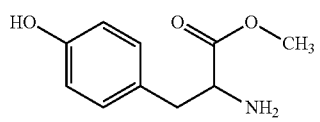
(AE62)
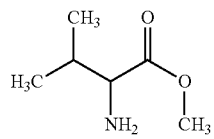

TABLE 2-continued
List of some CM of the invention.
(AE63)
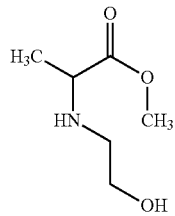
(AE64)
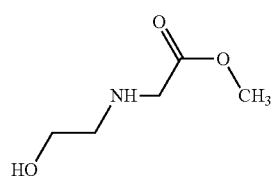
(AE65)
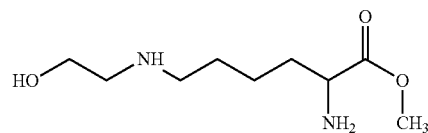
(AE66)
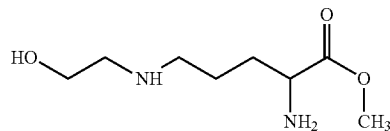
(AE67)
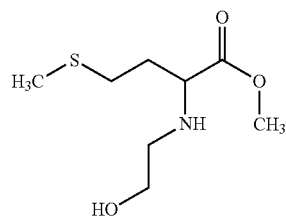
(AE68)
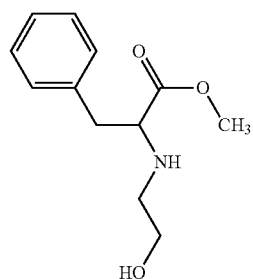

TABLE 2-continued

List of some CM of the invention.

(AE69)

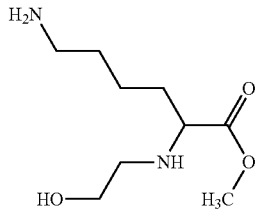

(AE70)

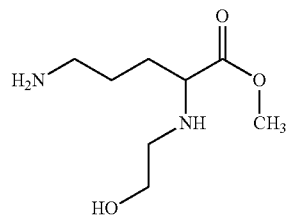

(AE71)

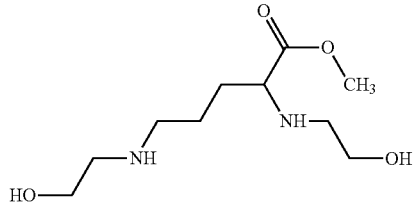

(AE72)

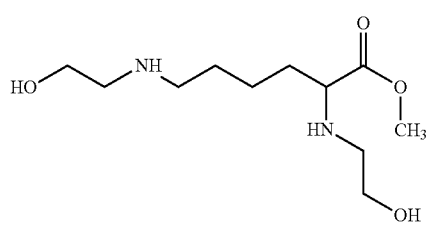

Important physicochemical parameters of the CM's are their pK values and their log D values, the latter being dependent on the charged state of the CM. The following tables 3-5 therefore provide the log D values at a pH that is substantially above the pK of the CM (uncharged state) and substantially below the pK of the CM (charged state). Some of the CM do comprise more than a single charged nitrogen base and both pK values and separate log D values and their increments are given for these structures. The numbering of the compounds is equivalent to that in table 2.

Table 3-5: pK values for some CM of the invention and their log D values in charged and uncharged form.

TABLE 3

| CM | pK1 | logD > pK | logD < pK | Δ log D |
|---|---|---|---|---|
| 1 | 8.28 | −1.21 | −4.31 | 3.1 |
| 2 | 4.34 | −0.92 | −2.92 | 2 |

TABLE 3-continued

| CM | pK1 | logD > pK | logD < pK | Δ log D |
|---|---|---|---|---|
| 3 | 5.56 | −1.92 | −3.92 | 2 |
| 4 | 8.97 | −1.08 | −4.18 | 3.1 |
| 5 | 8.08 | −0.59 | −3.69 | 3.1 |
| 6 | 5.08 | −0.95 | −4.04 | 3.09 |
| 7 | 5.5 | −0.39 | −3.49 | 3.1 |
| 8 | 4.39 | −0.15 | −2.14 | 1.99 |
| 9 |  | −0.43 | −0.43 | 0 |
| 10 | 5.45 | 0.18 | −2.92 | 3.1 |
| 11 | 2.81 | −1.17 | #NV | #NV |
| 12 | 2.64 | −1.17 | #NV | #NV |
| 13 | 7 | −1.49 | −5.17 | 3.68 |
| 14 | 4.35 | −0.33 | −2.33 | 2 |
| 15 | 9.9 | −0.33 | −2.33 | 2 |
| 16 | 6.54 | −1.86 | −4.96 | 3.1 |
| 17 | 3.69 | −0.33 | −2.32 | 1.99 |
| 18 | −0.27 | 0.75 | #NV | #NV |
| 19 | 7.18 | −0.16 | −2.66 | 2.5 |
| 20 | 2.47 | 0.32 | #NV | #NV |

TABLE 3-continued

| CM | pK1 | logD > pK | logD < pK | Δ log D |
|---|---|---|---|---|
| 21 | 11.26 | 0.37 | −2.73 | 3.1 |
| 22 | 10.03 | −0.23 | −2.23 | 2 |
| 23 pK1 | 10.33 | −1.23 | −4.09 | 2.86 |
| 23 pK2 | 4.8 | −4.09 | −5.33 | 1.24 |
| 24 | 10.9 | −1.08 | −3.08 | 2 |
| 25 | 9.7 | −0.72 | −3.82 | 3.1 |
| 26 | 7.06 | −0.48 | −2.62 | 2.14 |
| 27 | 5.23 | 0.73 | −1.77 | 2.5 |
| 28 | 1 | −0.28 | #NV | #NV |
| 29 | 1.29 | −0.33 | #NV | #NV |
| 30 | 2.34 | −0.77 | #NV | #NV |
| 31 | 8.97 | 0.93 | −2.17 | 3.1 |
| 32 pK1 | 9.9 | −1.17 | −4.1 | 2.93 |
| 32 pK2 | 5.3 | −4.1 | −5.27 | 1.17 |
| 33 | 10.87 | 1.38 | −1.72 | 3.1 |
| 40 | 6.58 | −0.74 | −3.83 | 3.09 |
| 41 | 6.95 | −0.6 | −3.7 | 3.1 |
| 42 | 6.58 | 0.55 | −2.55 | 3.1 |
| 43 | 4.13 | 1.21 | −1.85 | 3.06 |
| 44 | 2.82 | −1.25 | #NV | #NV |
| 45 | 2.93 | −0.69 | #NV | #NV |
| 46 | 5.94 | −1.02 | −4.09 | 3.07 |
| 47 | 5.31 | −2.55 | −5.65 | 3.1 |
| 48 | 6.78 | −0.63 | −3.13 | 2.5 |
| 49 | 9.79 | 0.49 | −2.61 | 3.1 |
| 50 | 8.93 | 0.16 | −1.84 | 2 |
| 51 pK1 | 9.57 | −0.64 | −3.7 | 3.06 |
| 51 pK2 | 4.21 | −3.7 | −4.74 | 1.04 |
| 52 | 9.74 | −1.95 | −3.94 | 1.99 |
| 53 | 8.47 | −1.58 | −4.68 | 3.1 |
| 54 | 6.13 | −1.3 | −3.31 | 2.01 |
| 55 | 5.01 | −0.46 | −2.89 | 2.50 |
| 56 | 9.04 | 1.06 | −2.04 | 3.1 |
| 57 pK1 | 9.27 | −0.45 | −3.5 | 3.05 |
| 57 pK2 | 3.48 | −3.5 | −4.55 | 1.05 |
| 58 |  | −3.08 | −3.08 | 0 |
| 59 | 3.33 | −1.4 | −4.5 | 3.1 |
| 60 | 5.16 | −1.21 | −4.3 | 3.09 |
| 61 | 4.36 | −1.21 | −4.3 | 3.09 |
| 62 | 3.83 | −2.09 | −5.2 | 3.11 |
| 63 | 5.34 | −1.9 | −5.02 | 3.12 |
| 64 pK1 | 8.69 | −1.93 | −5 | 3.07 |
| 64 pK2 | 4.12 | −5 | −6.02 | 1.02 |
| 65 | 4.92 | −0.57 | −3.66 | 3.09 |
| 66 | 5.31 | −0.39 | −3.49 | 3.1 |
| 67 | 4.92 | 0.55 | −2.54 | 3.09 |
| 68 | 3.28 | −2.03 | −5.1 | 3.07 |
| 69 | 6.21 | −0.61 | −3.11 | 2.5 |
| 70 | 5.53 | −0.9 | −3.98 | 3.08 |
| 71 | 6.6 | 0.39 | −1.61 | 2 |
| 72 | 8.41 | −1.52 | −3.55 | 2.03 |
| 73 | 8.33 | 0.36 | −2.74 | 3.1 |
| 74 | 6.44 | −1.36 | −4.46 | 3.1 |
| 75 | 4.1 | −1.05 | −3.04 | 1.99 |
| 76 |  | −3.99 | −3.99 | 0 |
| 77 | 7.37 | 0.92 | −2.18 | 3.1 |
| 78 | 3.49 | −1.04 | −4.1 | 3.06 |
| 79 |  | −2.25 | −2.25 | 0 |
| 80 | 3.67 | −1.73 | −4.75 | 3.02 |
| 81 pK1 | 7.38 | −1.62 | −4.5 | 2.88 |
| 81 pK2 | 5.51 | −4.5 | −5.71 | 1.21 |
| 82 pK1 | 8.35 | −0.79 | −3.8 | 3.01 |
| 82 pK2 | 6.48 | −3.8 | −4.87 | 1.07 |

TABLE 4

| CM | pK1 | logD > pK | logD < pK | Δ log D |
|---|---|---|---|---|
| N1 | 3.91 | −0.03 | −2.52 | 2.49 |
| N2 | 4.18 | −1.71 | −3.71 | 2 |
| N3 | 3.15 | −0.98 | −3.41 | 2.43 |
| N4 | −1.61 | −0.61 | #NV | #NV |
| N5 | −1.65 | −0.71 | #NV | #NV |
| N6 | 1 | −0.87 | #NV | #NV |
| N7 | 2.2 | −1.19 | #NV | #NV |
| A1 | 10.66 | −0.68 | −3.76 | 3.08 |
| A2 | 10.73 | −0.45 | −3.53 | 3.08 |
| A3 | 9.75 | 0.06 | −3.04 | 3.1 |
| A4 | 99 | −2.89 | −2.89 | 0 |
| A5 | 9.16 | −1.34 | −4.41 | 3.07 |
| A6 | 8.71 | −1.51 | −4.6 | 3.09 |
| A7 | 7.77 | −1.11 | −4.21 | 3.1 |
| A8 | 9.91 | −1.12 | −4.22 | 3.1 |
| A9 | 10.01 | −1.26 | −4.35 | 3.09 |
| A10 | 8.32 | −1.59 | −4.69 | 3.1 |
| A11 | 9.36 | −1.38 | −4.48 | 3.1 |
| A12 | 7.93 | −1.43 | −4.53 | 3.1 |
| A13 | 8.24 | −1.27 | −4.37 | 3.1 |

TABLE 5

| CM | pK1 | logD > pK | logD < pK | Δ log D |
|---|---|---|---|---|
| AE1 | 6.39 | −1.26 | −4.36 | 3.1 |
| AE2 | 6.21 | −0.38 | −2.69 | 2.31 |
| AE3 | 7.14 | −0.81 | −3.91 | 3.1 |
| AE4 | 7.05 | 0.37 | −2.7 | 3.07 |
| AE5 | 7.55 | −0.82 | −3.92 | 3.1 |
| AE6 | 7.52 | 0.5 | −2.57 | 3.07 |
| AE7 | 6.2 | −2.07 | −5.17 | 3.1 |
| AE8 | 6.14 | −0.77 | −3.86 | 3.09 |
| AE9 | 6.51 | −1.18 | −4.27 | 3.09 |
| AE10 | 6.6 | −0.55 | −3.63 | 3.08 |
| AE11 | 6.75 | −1.61 | −4.71 | 3.1 |
| AE12 | 6.79 | −0.24 | −3.32 | 3.08 |
| AE13 | 4.63 | −1.11 | −4.2 | 3.09 |
| AE14 | 5.9 | −0.65 | −3.75 | 3.1 |
| AE15 | 6.9 | −0.541 | −3.64 | 3.099 |
| AE16 | 6.75 | −0.32 | −3.42 | 3.1 |
| AE17 | 7.8 | −0.23 | −3.33 | 3.1 |
| AE18 | 9.28 | −0.39 | −3.48 | 3.09 |
| AE21 | 6.3 | −2.1 | −5.22 | 3.12 |
| AE22 | 6.11 | −0.58 | −3.65 | 3.07 |
| AE23 | 7.05 | −1.9 | −5.03 | 3.13 |
| AE24 | 6.95 | −0.59 | −3.67 | 3.08 |
| AE25 | 7.45 | −1.78 | −4.91 | 3.13 |
| AE26 | 7.42 | −0.46 | −3.53 | 3.07 |
| AE27 | 5.18 | −2.75 | −5.86 | 3.11 |
| AE28 | 5.75 | −1.46 | −4.54 | 3.08 |
| AE29 | 6.12 | −1.86 | −4.98 | 3.12 |
| AE30 | 6.22 | −1.23 | −4.32 | 3.09 |
| AE31 | 6.36 | −2.3 | −5.42 | 3.12 |
| AE32 | 6.4 | −0.92 | −4.01 | 3.09 |
| AE33 | 4.53 | −1.43 | −4.53 | 3.1 |
| AE34 | 5.8 | −1.36 | −4.48 | 3.12 |
| AE35 | 6.8 | −1.46 | −4.59 | 3.13 |
| AE36 | 6.52 | −1.51 | −4.6 | 3.09 |
| AE37 | 8.71 | −1.52 | −4.62 | 3.1 |
| AE38 | 9.17 | −1.61 | −4.7 | 3.09 |
| AE39 | 4.43 | −2.39 | −5.5 | 3.11 |
| AE40 | 5.58 | −2.59 | −5.76 | 3.17 |
| AE41 | 6.68 | −2.68 | −5.78 | 3.1 |
| AE42 | 6.29 | −2.73 | −5.82 | 3.09 |
| AE43 | 8.6 | −2.75 | −5.85 | 3.1 |
| AE44 | 9.36 | −2.83 | −5.93 | 3.1 |
| AE45 | 7.4 | −1.34 | −4.44 | 3.1 |
| AE46 | 8.67 | −1.44 | −4.54 | 3.1 |
| AE47 | 9.67 | −1.3 | −4.39 | 3.09 |
| AE48 | 7.87 | −0.99 | −4.08 | 3.09 |
| AE49 | 7.89 | −0.45 | −3.55 | 3.1 |
| AE50 pK1 | 13.37 | −2.15 | −4.01 | 1.86 |
| AE50 pK2 | 7.48 | −4.01 | −6.21 | 2.2 |
| AE51 | 7.98 | 0.42 | −2.67 | 3.09 |
| AE52 | 7.95 | 0.42 | −2.67 | 3.09 |
| AE53 pK1 | 10.46 | −1.35 | −3.4 | 2.05 |
| AE53 pK2 | 7.3 | −3.4 | −5.44 | 2.04 |
| AE54 | 6.96 | 0.07 | −3.03 | 3.1 |
| AE55 | 7.92 | 0.61 | −2.49 | 3.1 |
| AE56 | 7.92 | 0.08 | −3.02 | 3.1 |

TABLE 5-continued

| CM | pK1 | logD > pK | logD < pK | Δ log D |
|---|---|---|---|---|
| AE57 pK1 | 10.14 | −1.27 | −3.8 | 2.53 |
| AE57 pK2 | 6.87 | −3.8 | −5.37 | 1.57 |
| AE58 | 7.13 | 0.76 | −2.34 | 3.1 |
| AE59 | 9.19 | −0.6 | −3.7 | 3.1 |
| AE60 | 7.8 | 0.69 | −2.46 | 3.15 |
| AE61 | 7.36 | −0.03 | −3.08 | 3.05 |
| AE62 | 7.95 | −0.11 | −3.21 | 3.1 |
| AE63 | 6.41 | −0.72 | −3.82 | 3.1 |
| AE64 | 6.41 | −1.06 | −4.16 | 3.1 |
| AE65 pK1 | 9.67 | −1.65 | −4.1 | 2.45 |
| AE65 pK2 | 7.6 | −4.1 | −5.74 | 1.64 |
| AE66 pK1 | 9.51 | −1.57 | −4.1 | 2.53 |
| AE66 pK2 | 7.14 | −4.1 | −5.67 | 1.57 |
| AE67 | 5.99 | 0.33 | −2.77 | 3.1 |
| AE68 | 6.02 | 0.94 | −2.16 | 3.1 |
| AE69 pK1 | 10.46 | −1.09 | −3.8 | 2.71 |
| AE69 pK2 | 6.17 | −3.8 | −5.17 | 1.37 |
| AE70 pK1 | 10.14 | −1.01 | −3.66 | 2.65 |
| AE70 pK2 | 5.72 | −3.66 | −5.1 | 1.44 |
| AE71 pK1 | 9.51 | −1.31 | −4 | 2.69 |
| AE71 pK2 | 6.09 | −4 | −5.4 | 1.4 |
| AE72 pK1 | 9.67 | −1.38 | −3.9 | 2.52 |
| AE72 pK2 | 6.32 | −3.9 | −5.48 | 1.58 |

Architecture of Zwitterionic Nucleic Acids

Nucleotides of the invention form zwitterionic structures wherein the CM undergoes ion-pairing with the negatively charged internucleoside linkage. In many embodiments, the CM is therefore located in close spatial proximity to the internucleoside linkage. Preference is given to structures wherein the CM is grafted on position C1, C2 or C4 of the nucleoside backbone, as illustrated in the structures (CM1) to (CM3) below. With more preference, the CM is grafted on the C2 position of the nucleotide as in structure (CM1). IPN's are often used to form nucleic acids and are therefore drawn here in their chain form.

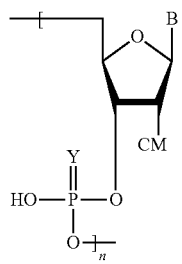

(CM1)

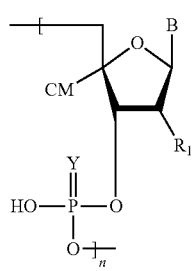

(CM2)

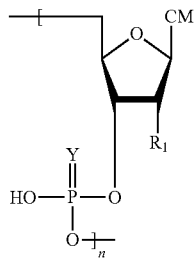

(CM3)

The structures (CM1) to (CM3) represent nucleotides of a nucleic acid; n>=2, B is any nucleobase selected from adenine, guanine, thymine, cytosine or uracile; Y is oxygen or sulphur, R1 can be H, OH, F, —O—CH3, —O—CH2-CH3, —O—CH2-CH2-O—CH3, —SH, —S—CH3, —S—CH2-CH3, —S—CH2-CH2-O—CH3 and CM is defined as above.

As mentioned above, the formation of the zwitterion is guided by the availability of the charged cation and depends on the pK of the CM and the following analysis shall thus illustrate this relationship.

For the analysis, the structure (CM4) to (CM7) were used, wherein (CM1) is present in its abasic form, Y is oxygen and the CM is the ethoxy-homologue of compound (A4), the compounds (A5), (48) or (AE34).

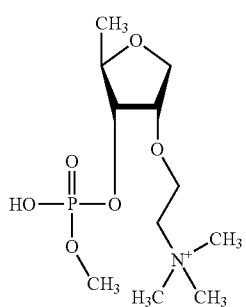

(CM4)

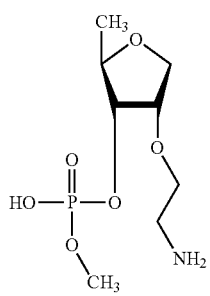

(CM5)

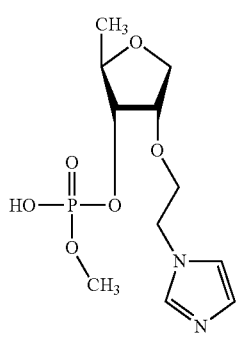

(CM6)

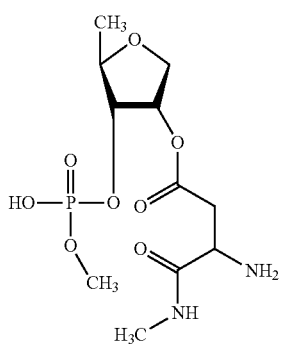

(CM7)

Introduction of the zwitterionic structure leads to a substantial change of the log D profile of these nucleic acids. As shown in FIG. 1, the unsubstituted phosphoribose backbone of all structures (CM4) through to (CM7) becomes gradually less hydrophilic at low values of pH (more acidic than pH5). Insertion of a constantly charged CM as in (CM4) leads to instant zwitterion formation and results in a higher, less polar value for log D. However, (CM4) and related structures do not respond to any change in pH. CM's with gradually lower values of pK, such as (CM5)>(CM6)>(CM7) do form zwitterionic structures, but now in a pH-sensitive manner. The curves have the highest increment at the pK of the respective CM (see also FIG. 1). Nucleic acids having the structural unit (CM5), although being responsive towards pH, are not preferred for use within a pH range between 7.4 and 4 since the response falls outside this range. Nucleic acids comprising the structural elements (CM4) or (CM5) therefore need additional elements that confer the required pH response in between pH4 and pH7.4 and can be further substituted with one or more TEE to yield nucleotides of IPN1 type. Structure (CM6) yields a substantial and structure (CM7) gives a complete response of log D within this range of pH values, these subunits can be used to construct nucleotides of IPN2 or IPN3 type.

FIG. 1 also allows the deduction of some quantitative relationships. For pH>>pK (uncharged CM) the sum of individual log D is fairly predictive for the log D of the complete structure, as demonstrated in table 6.

TABLE 6

Quantitative analysis of logD for structural elements of zwitterionic nucleic acids, pH >> pK.

| Structure | Backbone | CM (uncharged) | BB + CM | logD (FIG. 1) |
|---|---|---|---|---|
| CM4 | −4.52 | Not defined | | |
| CM5 | −4.52 | −1.34 | −5.86 | −5.42 |
| CM6 | −4.52 | −0.63 | −5.15 | −5.19 |
| CM7 | −4.52 | −1.36 | −5.88 | −5.46 |

At pH<<pK zwitterion formation occurs between the CM and the internucleoside linkage, thereby reducing the log D of the combined moiety by about 3.5 to 5 units, as shown in the analysis in table 7:

TABLE 7

Quantitative analysis of logD for structural elements of zwitterionic nucleic acids, pH << pK.

| Structure | Backbone | CM (charged) | BB + CM | logD (FIG. 1) | Delta |
|---|---|---|---|---|---|
| CM4 | −4.52 | −3.7 | −8.22 | −3.24 | −4.98 |
| CM5 | −4.52 | −4.41 | −8.93 | −4.44 | −4.49 |
| CM6 | −4.52 | −3.13 | −7.65 | −4.19 | −3.46 |
| CM7 | −4.52 | −4.48 | −9 | −4.46 | −4.54 |

As shown in FIG. 1, the net pH-dependent amplitude for the zwitterion formation in these structures is about 1 unit of log D.

The analysis also reveals a limitation of structures (CM4) to (CM7): the mere addition of a CM often increases the overall hydrophilicity, hence making the molecule even less permeable than its parent compound DNA or RNA. Some molecules like the 2'IME-nucleotides in Prakash et al. (in Curr Top. Med. Chem. 2007 (7), 641-649) or the zwitterionic nucleic acids of Teplova et al. (in PNAS 1999 (96), 14240-14245) are thus not functional in terms of enhanced membrane permeability.

It is therefore important for practicing this invention to either select CM's with a high intrinsic log D or to further add hydrophobic moieties or TEE's to cure such defect and the following description provides limitations for the log D values of IPN's as well as algorithms that return a range of preferred sizes for the hydrophobic moieties. For numerous of specific structures, specific preferred values are presented within this disclosure. For such calculations, the PCT/EP2007/011188 (also called REF1 herein) teaches that any additional —CH2- moiety provides a log D of about +0.5 thus providing guidance for the estimation of the size of such hydrophobic additions. REF1 also provides structural impacts for numerous other building blocks and any different chemical representations can easily be calculated from such information.

It has been mentioned that zwitterion formation may occur between the CM and the internucleoside linkage in 3' position as well as in 5' position of the nucleotide, which provides some ambiguity in the assignment of an IPN structure towards a specific nucleotide. Most structures in this disclosure have been drawn with the internucleoside linkage in 3' position, but this is not limiting the teachings of this invention towards such architecture by any means. Instead, the structures (CM1) to (CM3) can be drawn as their isomers (CM8) to (CM10) as shown below and such isomer configuration can be applied to the other structures throughout this disclosure.

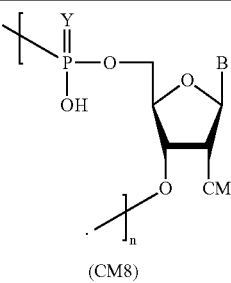

(CM8)

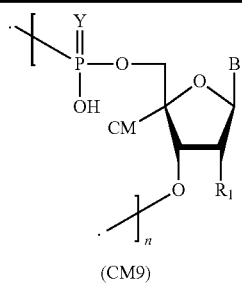

(CM9)

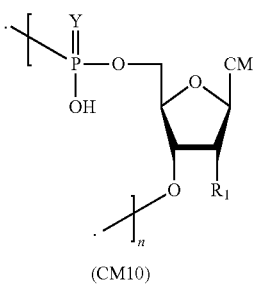

(CM10)

The structures (CM8) to (CM10) represent the isomeric IPN's to (CM1) to (CM3), respectively and monomers of such IPN in nucleic acids are shown here; n >= 2, B is any nucleobase selected from adenine, guanine, thymine, cytosine or uracile; Y is oxygen or sulphur, R1 can be H, OH, F, —O—CH3, —O—CH2—CH3, —O—CH2—CH2—O—CH3, —SH, —S—CH3, —S—CH2—CH3, —S—CH2—CH2—O—CH3 and CM is defined as above.

IPN 2 Structures

The description given so far is sufficient to construct complete nucleotides as IPN2 structures. The preferred internucleoside linkage is of phosphodiester, phosphothioate, or phosphodithioate type, but other linkages can be used as long as they provide a negative charge. In preferred embodiments of such structures, the pK of the CM is between 4 and 7.5, more preferred is a pK between 5 and 6.5.

The core architecture of an IPN2 nucleotide is presented in (CM1) to (CM3).

In most aspects, the log D(pH4) of an IPN2 nucleotide is higher than −2, in preferred aspects this value is between −1 and +3 and in some aspects it is greater than 3. Said log D refers to the chain form for the IPN2 nucleotide and represents the monomer increment per nucleotide, it is different from the IPN2 monomer itself mainly due to the presence of the second charge at the phosphate group.

The log D of IPN2 structures can be considered as a composite from (i) the backbone elements internucleoside linkage and nucleoside sugar, (ii) the nucleobases, if present as in (CM1) and (CM2), (iii) the CM and (iv) the pH dependent zwitterion formation between CM and internucleoside linkage.

Quantitative estimates for these elements have been presented above, approximate values for (i) are −2 to −3; (ii) is pH dependent and about −1.4 at pH 7.4 and −1.8 at pH4; values for (iii) are listed in tables 3 to 5 for the unprotonated form at pH>>pK and (iv) is about +1 for the zwitterion formation. In many cases of IPN2 structures, the contribution of (iv) will be absent at pH7.4 and present at pH4 and this pH-induced increase in log D overcompensates the pH-induced decrease of log D from the nucleobases.

The following table 8 presents specific composite log D's for some of the IPN2 structures comprising the core unit of (CM1) or (CM2) using the data presented in the tables 3 to 5 above. It is of course possible to analyze structures of different chemical origin in the same way; this analysis is illustrating, but not limiting the teachings of this invention.

For comparison, one can calculate the composite log D of an average nucleotide as the sum of its components: −2.5 as average for the backbone and −1.8 for a statistical nucleobases at pH4 or the respective value at pH7.4, the results are given in the first line of table 8. The composite log D for IPN2 structures at pH7.4 includes the CM, which at pH4 further includes the interaction gain of 1 for the zwitterion formation.

For some structures listed in table 8, the log D (pH4) of the composite is already close to the preferred range of log D (pH4)>−2 and these structures already have a substantially reduced hydrophilicity.

In many cases, the additional presence of a hydrophobic moiety is beneficial for the membrane permeability of the substance and the last two columns of table 8 identify compound specific ranges of such additions and return a preferred number of carbon atoms in such hydrophobic segment.

Further preferred IPN2 structures therefore comprise a hydrophobic moiety, said moiety essentially comprising between 2 and 20 carbon atoms. REF1 teaches that the specific chemical configuration of such hydrophobic moieties has little impact on the log D contribution; REF1 has also analyzed the impact of potential substitutions to such hydrophobic moieties. In many cases the specific position of the hydrophobic moiety on the core structures (CM1)-(CM3) may also vary without substantial impact to the physicochemical parameters.

TABLE 8

Physicochemical analysis of some specific IPN2 structures having a pK between 5 and 7. CM means the compound as in table 2, all other headings are described in the text.

| CM | pK | logD > pK | composite logD pH 4 | composite logD pH 7.4 | # C atoms for logD −1 | # C atoms for logD +3 |
|---|---|---|---|---|---|---|
| none | none | 0 | −4.3 | −3.9 | | |
| 3 | 5.56 | −1.92 | −5.22 | −5.82 | 8 | 16 |
| 6 | 5.08 | −0.95 | −4.25 | −4.85 | 6 | 14 |
| 7 | 5.5 | −0.39 | −3.69 | −4.29 | 5 | 13 |
| 10 | 5.45 | 0.18 | −3.12 | −3.72 | 4 | 12 |
| 13 | 7 | −1.49 | −4.79 | −5.39 | 7 | 15 |
| 16 | 6.54 | −1.86 | −5.16 | −5.76 | 8 | 16 |
| 27 | 5.23 | 0.73 | −2.57 | −3.17 | 3 | 11 |
| 32 pK2 | 5.3 | −4.1 | −7.4 | −8 | 12 | 20 |
| 40 | 6.58 | −0.74 | −4.04 | −4.64 | 6 | 14 |
| 41 | 6.95 | −0.6 | −3.9 | −4.5 | 5 | 13 |
| 42 | 6.58 | 0.55 | −2.75 | −3.35 | 3 | 11 |
| 46 | 5.94 | −1.02 | −4.32 | −4.92 | 6 | 14 |
| 47 | 5.31 | −2.55 | −5.85 | −6.45 | 9 | 17 |
| 48 | 6.78 | −0.63 | −3.93 | −4.53 | 5 | 13 |
| 54 | 6.13 | −1.3 | −4.6 | −5.2 | 7 | 15 |
| 55 | 5.01 | −0.46 | −3.76 | −4.36 | 5 | 13 |
| 60 | 5.16 | −1.21 | −4.51 | −5.11 | 7 | 15 |
| 63 | 5.34 | −1.9 | −5.2 | −5.8 | 8 | 16 |
| 66 | 5.31 | −0.39 | −3.69 | −4.29 | 5 | 13 |
| 69 | 6.21 | −0.61 | −3.91 | −4.51 | 5 | 13 |
| 70 | 5.53 | −0.9 | −4.2 | −4.8 | 6 | 14 |
| 71 | 6.6 | 0.39 | −2.91 | −3.51 | 3 | 11 |
| 74 | 6.44 | −1.36 | −4.66 | −5.26 | 7 | 15 |
| 81 pK2 | 5.51 | −4.5 | −7.8 | −8.4 | 13 | 21 |
| 82 pK2 | 6.48 | −3.8 | −7.1 | −7.7 | 12 | 20 |
| AE1 | 6.39 | −1.26 | −4.56 | −5.16 | 7 | 15 |
| AE2 | 6.21 | −0.38 | −3.68 | −4.28 | 5 | 13 |
| AE7 | 6.2 | −2.07 | −5.37 | −5.97 | 8 | 16 |
| AE8 | 6.14 | −0.77 | −4.07 | −4.67 | 6 | 14 |
| AE9 | 6.51 | −1.18 | −4.48 | −5.08 | 6 | 14 |
| AE10 | 6.6 | −0.55 | −3.85 | −4.45 | 5 | 13 |
| AE11 | 6.75 | −1.61 | −4.91 | −5.51 | 7 | 15 |
| AE12 | 6.79 | −0.24 | −3.54 | −4.14 | 5 | 13 |
| AE14 | 5.9 | −0.65 | −3.95 | −4.55 | 5 | 13 |
| AE15 | 6.9 | −0.541 | −3.841 | −4.441 | 5 | 13 |

TABLE 8-continued

Physicochemical analysis of some specific IPN2 structures having a pK between 5 and 7. CM means the compound as in table 2, all other headings are described in the text.

IPN2 moieties

| CM | pK | composite logD > pK | composite logD pH 4 | composite logD pH 7.4 | # C atoms for logD −1 | # C atoms for logD +3 |
|---|---|---|---|---|---|---|
| AE16 | 6.75 | −0.32 | −3.62 | −4.22 | 5 | 13 |
| AE21 | 6.3 | −2.1 | −5.4 | −6 | 8 | 16 |
| AE22 | 6.11 | −0.58 | −3.88 | −4.48 | 5 | 13 |
| AE24 | 6.95 | −0.59 | −3.89 | −4.49 | 5 | 13 |
| AE27 | 5.18 | −2.75 | −6.05 | −6.65 | 10 | 18 |
| AE28 | 5.75 | −1.46 | −4.76 | −5.36 | 7 | 15 |
| AE29 | 6.12 | −1.86 | −5.16 | −5.76 | 8 | 16 |
| AE30 | 6.22 | −1.23 | −4.53 | −5.13 | 7 | 15 |
| AE31 | 6.36 | −2.3 | −5.6 | −6.2 | 9 | 17 |
| AE32 | 6.4 | −0.92 | −4.22 | −4.82 | 6 | 14 |
| AE34 | 5.8 | −1.36 | −4.66 | −5.26 | 7 | 15 |
| AE35 | 6.8 | −1.46 | −4.76 | −5.36 | 7 | 15 |
| AE36 | 6.52 | −1.51 | −4.81 | −5.41 | 7 | 15 |
| AE40 | 5.58 | −2.59 | −5.89 | −6.49 | 9 | 17 |
| AE41 | 6.68 | −2.68 | −5.98 | −6.58 | 9 | 17 |
| AE42 | 6.29 | −2.73 | −6.03 | −6.63 | 10 | 18 |
| AE54 | 6.96 | 0.07 | −3.23 | −3.83 | 4 | 12 |
| AE57 pK2 | 6.87 | −3.8 | −7.1 | −7.7 | 12 | 20 |
| AE63 | 6.41 | −0.72 | −4.02 | −4.62 | 6 | 14 |
| AE64 | 6.41 | −1.06 | −4.36 | −4.96 | 6 | 14 |
| AE67 | 5.99 | 0.33 | −2.97 | −3.57 | 3 | 11 |
| AE68 | 6.02 | 0.94 | −2.36 | −2.96 | 2 | 10 |
| AE69 pK2 | 6.17 | −3.8 | −7.1 | −7.7 | 12 | 20 |
| AE70 pK2 | 5.72 | −3.66 | −6.96 | −7.56 | 11 | 19 |
| AE71 pK2 | 6.09 | −4 | −7.3 | −7.9 | 12 | 20 |
| AE72 pK2 | 6.32 | −3.9 | −7.2 | −7.8 | 12 | 20 |

To further illustrate, but not limit the teachings of this invention, the following table 9 presents some more specific chemical representations for IPN2 structures in nucleic acids, wherein Y is oxygen or sulphur, B represents any of the nucleobases or is absent, the index n denotes the length of the nucleic acid and n is 2 or greater and i denotes the length of an alkyl chain which here represents the hydrophobic moiety, (i−1) preferably falls within the range specified in table 8 for the respective compounds. More than one hydrophobic moiety can be used in the such cases the preferred range for their size indices k and j shall be selected to meet k+j=i−1.

From the IPN2 structures shown below it becomes clear that the position of a given CM at the nucleoside sugar may vary and that some CM's can be inserted in different orientations as in the isomers IPN2-5/IPN2-6 or IPN2-13/IPN2-14 or IPN2-15/IPN2-16. Also, the position of the hydrophobic element may vary, as shown in IPN2-10 and IPN2-11 and the position of the graft may be variable, as seen in IPN2-17 or IPN2-18. Eventually, independent substitutions of the hydrophobic moiety and the CM are possible as shown in IPN2-19 through to IPN2-24.

TABLE 9

Specific representations of IPN2 structures.

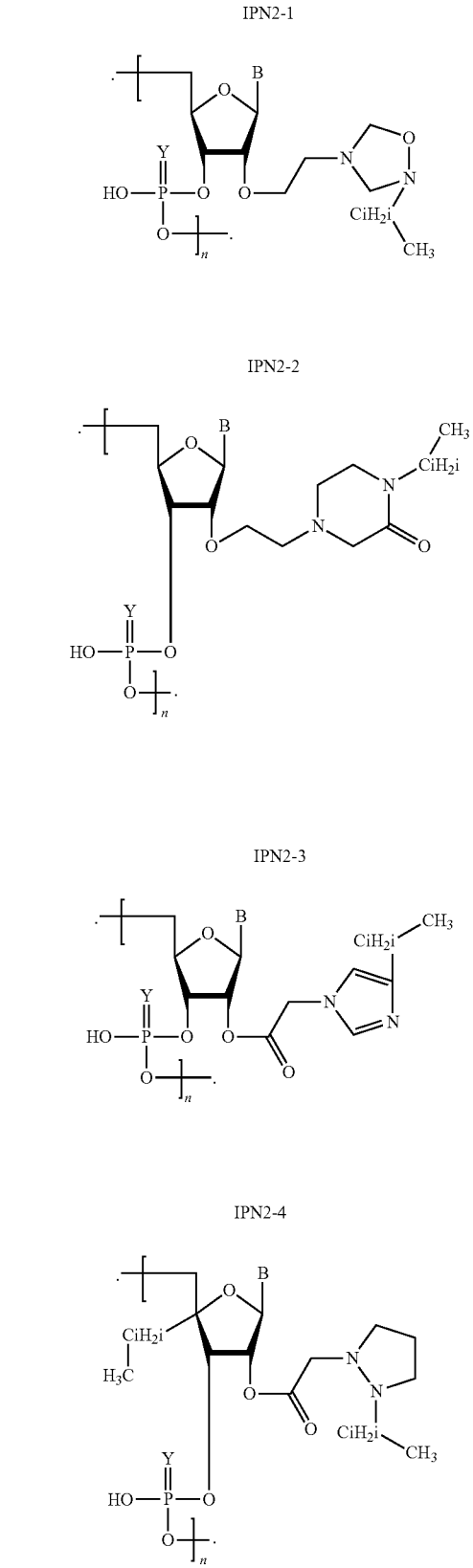

IPN2-1

IPN2-2

IPN2-3

IPN2-4

TABLE 9-continued
Specific representations of IPN2 structures.
IPN2-5
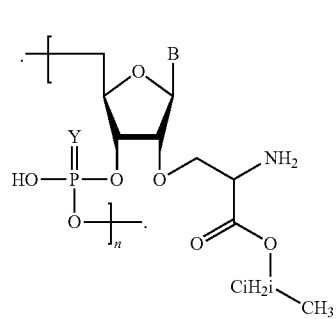
IPN2-6
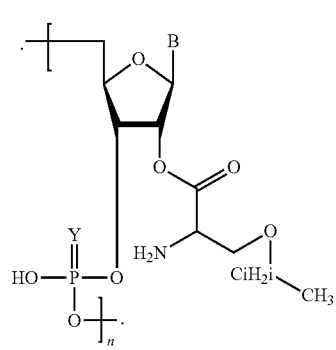
IPN2-7
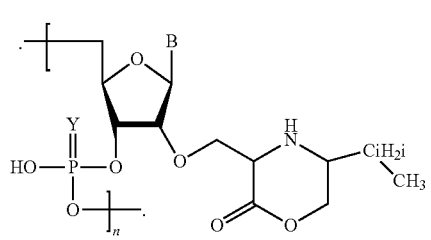
IPN2-8
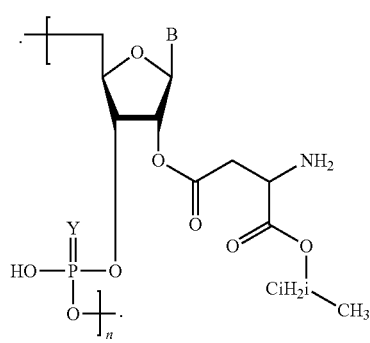
TABLE 9-continued
Specific representations of IPN2 structures.
IPN2-9
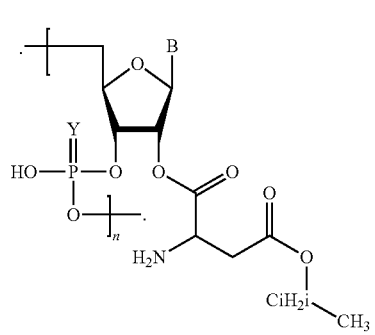
IPN2-10
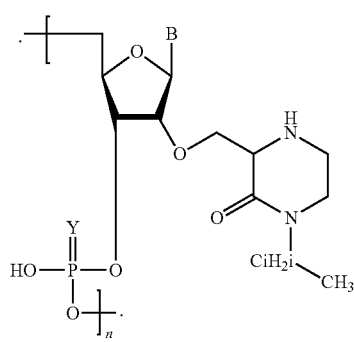
IPN2-11
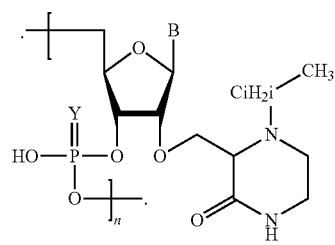
IPN2-12
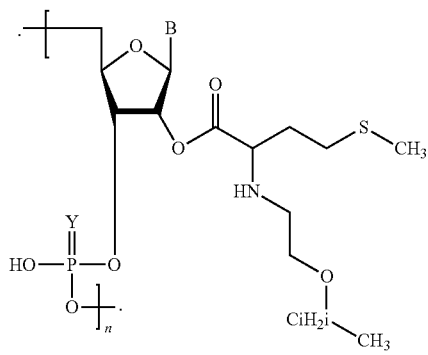

TABLE 9-continued
Specific representations of IPN2 structures.
IPN2-13
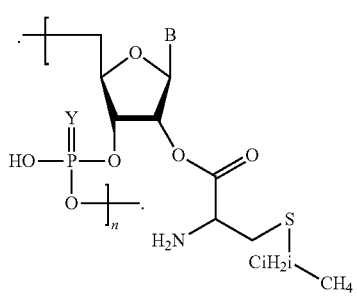
IPN2-14
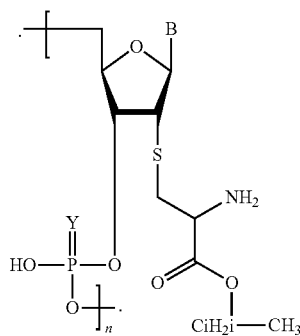
IPN2-15
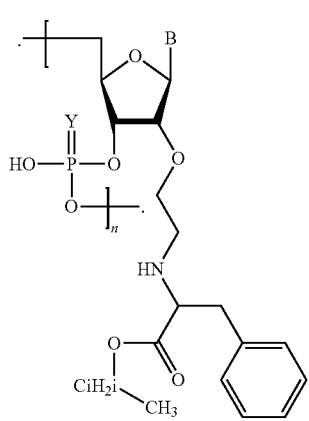
TABLE 9-continued
Specific representations of IPN2 structures.
IPN2-16
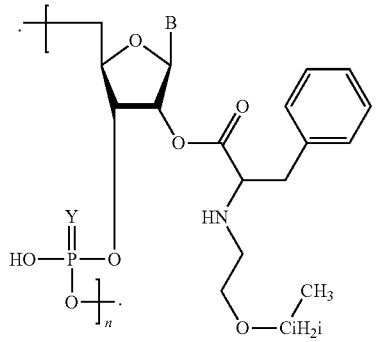
IPN2-17
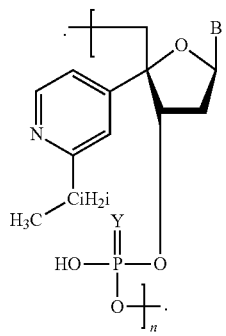
IPN2-18
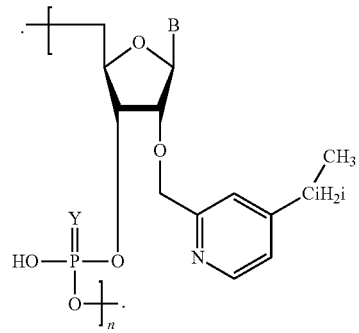
IPN2-19
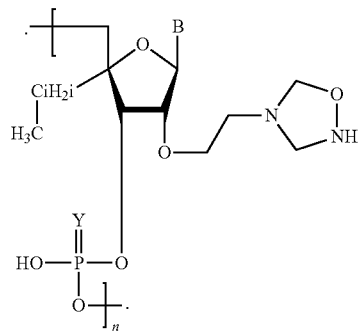

TABLE 9-continued

Specific representations of IPN2 structures.

IPN2-20

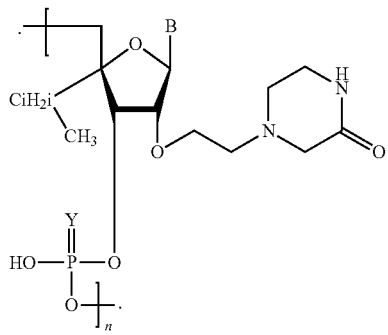

IPN2-21

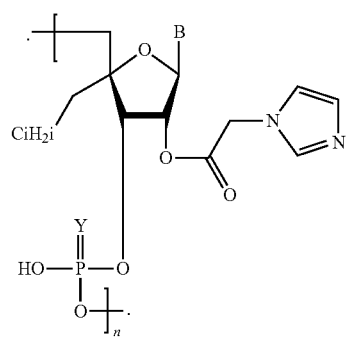

IPN2-22

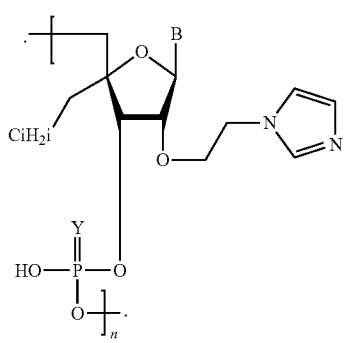

IPN2-23

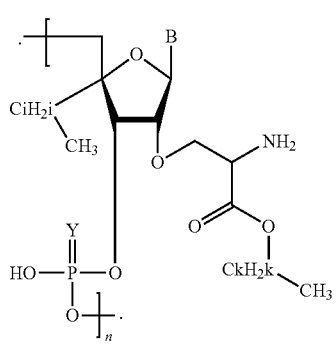

TABLE 9-continued

Specific representations of IPN2 structures.

IPN2-24

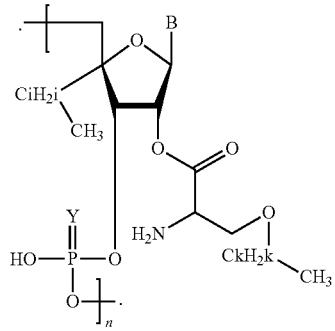

As disclosed above, the architecture of nucleic acids comprising the inventive IPN structures may vary and different degrees of substitution of native nucleic acids with IPN structures are possible. Also, such substitutions may be concentrated on specific sites within a nucleic acid, e.g. at one or both flanks of the sequence, at the center part of such sequence or they might be dispersed throughout the sequence. A known design in the art is a "gapmer", wherein modified sequences at the flanks of an oligonucleotide encompass an unmodified or differently modified sequence in a center piece.

The table 10 gives calculated log D values for 20mer oligonucleotides having a degree of substitution of 50% and such log D values have been calculated for pH4 and pH7.4 and for different values of i, the length indicator for the hydrophobic element. For comparison, the log D (pH7.4) of an unmodified sequence of the same type is −81, that of pH4 is −89. The standard assumptions giving above for log D of the internucleoside linkage, nucleobases and zwitterionic interaction were used.

Introduction of IPN2 elements into an oligonucleotide, even at a limited degree of substitution leads to substantial improvements in log D and preferred oligonucleotides having a log D>−60 are highlighted in the table 10. Also, the IPN2 substitutions minimize or even reverse the pH-induced decrease of log D at low values of pH. In a third aspect, this analysis gives additional guidance on the number of carbon atoms (i) in the hydrophobic element that may be present in IPN2 structures when used in nucleic acids at the given degree of substitution. While i=12 yields preferred structures in almost any case, even the short element with i=8 is sufficient for most species analyzed here. Even more so, some species achieve substantial improvements in log D even with i=4.

TABLE 10 logD predictions for 20mers of oligonucleotides comprising 50% IPN2 structures. The CM means the CM described in table 2 herein.
20mer oligonucleotides, 50% substitution with IPN2

| | i = 4 | | i = 8 | | i = 12 | |
|---|---|---|---|---|---|---|
| CM | pH 4 | pH 7.4 | pH 4 | pH 7.4 | pH 4 | pH 7.4 |
| 3 | −78 | −80 | −58 | −60 | −38 | −40 |
| 6 | −69 | −71 | −49 | −51 | −29 | −31 |
| 7 | −63 | −65 | −43 | −45 | −23 | −25 |
| 10 | −57 | −59 | −37 | −39 | −17 | −19 |
| 13 | −74 | −76 | −54 | −56 | −34 | −36 |
| 16 | −78 | −80 | −58 | −60 | −38 | −40 |

TABLE 10-continued logD predictions for 20mers of oligonucleotides comprising 50% IPN2 structures. The CM means the CM described in table 2 herein.

20mer oligonucleotides, 50% substitution with IPN2

| CM | i = 4 | | i = 8 | | i = 12 | |
|---|---|---|---|---|---|---|
| | pH 4 | pH 7.4 | pH 4 | pH 7.4 | pH 4 | pH 7.4 |
| 27 | −52 | −54 | −32 | −34 | −12 | −14 |
| 32 pK2 | −100 | −102 | −80 | −82 | −60 | −62 |
| 40 | −66 | −68 | −46 | −48 | −26 | −28 |
| 41 | −65 | −67 | −45 | −47 | −25 | −27 |
| 42 | −54 | −56 | −34 | −36 | −14 | −16 |
| 46 | −69 | −71 | −49 | −51 | −29 | −31 |
| 47 | −85 | −87 | −65 | −67 | −45 | −47 |
| 48 | −65 | −67 | −45 | −47 | −25 | −27 |
| 54 | −72 | −74 | −52 | −54 | −32 | −34 |
| 55 | −64 | −66 | −44 | −46 | −24 | −26 |
| 60 | −71 | −73 | −51 | −53 | −31 | −33 |
| 63 | −78 | −80 | −58 | −60 | −38 | −40 |
| 66 | −63 | −65 | −43 | −45 | −23 | −25 |
| 69 | −65 | −67 | −45 | −47 | −25 | −27 |
| 70 | −68 | −70 | −48 | −50 | −28 | −30 |
| 71 | −55 | −57 | −35 | −37 | −15 | −17 |
| 74 | −73 | −75 | −53 | −55 | −33 | −35 |
| 81 pK2 | −104 | −106 | −84 | −86 | −64 | −66 |
| 82 pK2 | −97 | −99 | −77 | −79 | −57 | −59 |
| AE1 | −72 | −74 | −52 | −54 | −32 | −34 |
| AE2 | −63 | −65 | −43 | −45 | −23 | −25 |
| AE7 | −80 | −82 | −60 | −62 | −40 | −42 |
| AE8 | −67 | −69 | −47 | −49 | −27 | −29 |
| AE9 | −71 | −73 | −51 | −53 | −31 | −33 |
| AE10 | −65 | −67 | −45 | −47 | −25 | −27 |
| AE11 | −75 | −77 | −55 | −57 | −35 | −37 |
| AE12 | −61 | −63 | −41 | −43 | −21 | −23 |
| AE14 | −66 | −68 | −46 | −48 | −26 | −28 |
| AE15 | −64 | −66 | −44 | −46 | −24 | −26 |
| AE16 | −62 | −64 | −42 | −44 | −22 | −24 |
| AE21 | −80 | −82 | −60 | −62 | −40 | −42 |
| AE22 | −65 | −67 | −45 | −47 | −25 | −27 |
| AE24 | −65 | −67 | −45 | −47 | −25 | −27 |
| AE27 | −87 | −89 | −67 | −69 | −47 | −49 |
| AE28 | −74 | −76 | −54 | −56 | −34 | −36 |
| AE29 | −78 | −80 | −58 | −60 | −38 | −40 |
| AE30 | −71 | −73 | −51 | −53 | −31 | −33 |
| AE31 | −82 | −84 | −62 | −64 | −42 | −44 |
| AE32 | −68 | −70 | −48 | −50 | −28 | −30 |
| AE34 | −73 | −75 | −53 | −55 | −33 | −35 |
| AE35 | −74 | −76 | −54 | −56 | −34 | −36 |
| AE36 | −74 | −76 | −54 | −56 | −34 | −36 |
| AE40 | −85 | −87 | −65 | −67 | −45 | −47 |
| AE41 | −86 | −88 | −66 | −68 | −46 | −48 |
| AE42 | −86 | −88 | −66 | −68 | −46 | −48 |
| AE54 | −58 | −60 | −38 | −40 | −18 | −20 |
| AE57 pK2 | −97 | −99 | −77 | −79 | −57 | −59 |
| AE63 | −66 | −68 | −46 | −48 | −26 | −28 |
| AE64 | −70 | −72 | −50 | −52 | −30 | −32 |
| AE67 | −56 | −58 | −36 | −38 | −16 | −18 |
| AE68 | −50 | −52 | −30 | −32 | −10 | −12 |
| AE69 pK2 | −97 | −99 | −77 | −79 | −57 | −59 |
| AE70 pK2 | −96 | −98 | −76 | −78 | −56 | −58 |
| AE71 pK2 | −99 | −101 | −79 | −81 | −59 | −61 |
| AE72 pK2 | −98 | −100 | −78 | −80 | −58 | −60 |

IPN1 Structures.

The description given so far is also sufficient to construct complete nucleic acid monomer units as IPN1 structures. The preferred internucleoside linkage is of phosphodiester, phosphothioate, or phosphodithioate type, but other linkages can be used as long as they provide a negative charge. IPN1 structures comprise a CM that is substantially charged at pH7.5, that is, the pK of such structure is equal or greater than 7.5 and in some embodiments the CM is a constantly charged cationic moiety comprising an ammonium or guanidinium group without an explicit value for pK. Besides their CM, IPN1 structures further comprise a TEE.

The core architecture of some IPN1 nucleic acid monomers is presented in table 11.

TABLE 11

Core structures of IPN1 elements (IPN1-1)

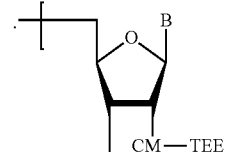

(IPN1-2)

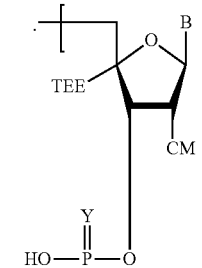

(IPN1-3)

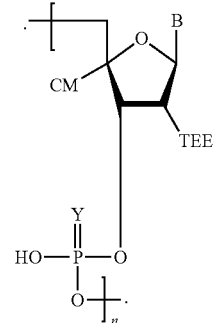

(IPN1-4)

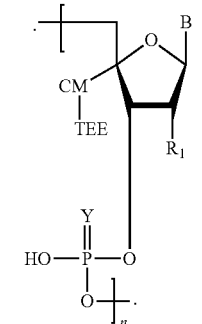

TABLE 11-continued

Core structures of IPN1 elements

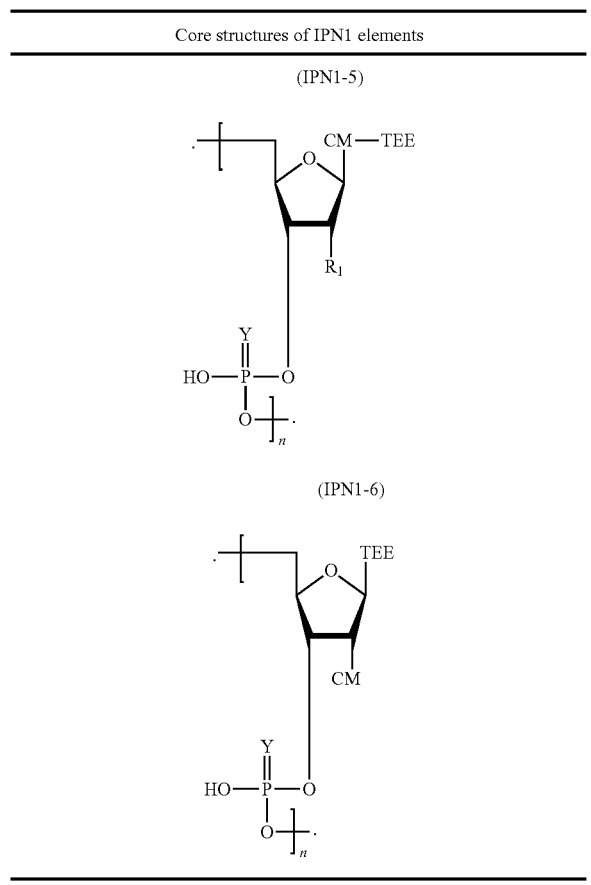

In many aspects of the inventive IPN1 structures, the weak acid of the TEE is a carboxylic acid.

In preferred embodiments of IPN1 structures, the hydrophobic element of the TEE is directly attached to the CM as in IPN1-1, IPN1-4 or IPN1-5.

In most aspects, the log D(pH4) of an IPN1 nucleotide is higher than −2, in preferred aspects this value is between −1 and +3 and in some aspects it is greater than 3. Said log D refers to the chain form for the IPN1 nucleotide and represents the monomer increment per nucleotide, it is different from the IPN1 monomer itself mainly due to the presence of the second charge at the phosphate group.

The log D of IPN1 structures can be considered as a composite from (i) the backbone elements internucleoside linkage and nucleoside sugar, (ii) the nucleobases itself, if present, (iii) the CM and (iv) the zwitterion formation between CM and internucleoside linkage and (v) the TEE. Quantitative estimates for the composite elements have been presented above for IPN2 structures and approximate values for (i) are −2 to −3; (ii) is pH dependent and about −1.4 at pH 7.4 and −1.8 at pH4; values for (iii) are listed in tables 3 to 5 for the unprotonated form at pH>pK; the log D for the hypothetical uncharged form of the quarternized ammonium groups were extrapolated as log D(protonated)+3.1; this increment has been deduced from most of the differences in other CM having a real pK. (iv) is about +1 for the zwitterion formation. For (v), the contribution of the TEE can be segmented into the contribution of the hydrophilic moiety and the hydrophobic moiety to simplify the assignment of the number of elements in the hydrophobic moiety. Data provided in PCT/EP2007/011188 for the relationship between the number of methylene groups in carboxylic acids and the resulting log D values can be extrapolated to conclude the contributions of this charged element. The resulting values are −0.9 for the uncharged and −3.4 for the charged state of this element. The TEE also comprises a hydrophobic element, since without such element the net contribution of the charged group to the log D is negative. For practicing this invention, the global log D of the IPN structure is of importance, it is less important whether the CM and its hydrophobic additions or the TEE and its hydrophobic element contribute the required hydrophobicity. In many embodiments of the IPN1 and IPN3 structures this hydrophobic moiety can be common structure of the CM and the TEE.

The following table 12 presents specific composite log D's for some of the IPN1 structures comprising any of the core units IPN1-1 through to IPN1-4 using the data presented in the tables 3 to 5 above. It is of course possible to analyze structures of different chemical origin in the same way; this analysis is illustrating, but not limiting the teachings of this invention. The composite log D values do comprise the elements (i) to (v) presented before and are given for both the neutral pH and an acidic pH; these composite log D's are extrapolated for species wherein the hydrophobic moiety of the TEE is absent. This allows identifying preferred ranges for the size of said hydrophobic elements and said ranges are given in the last two columns of this table 12 for cases where the hydrophobic elements are methylene groups. Preferred hydrophobic moieties comprise between 3 and 22 carbon atoms. REF1 teaches that the specific chemical configuration of such hydrophobic moieties has little impact on the log D contribution; REF1 has also analyzed the impact of potential substitutions to such hydrophobic moieties. In many cases the specific position of the hydrophobic moiety on the core structures (IPN1-1)-(IPN1-4) may also vary without substantial impact to the physicochemical parameters.

TABLE 12

Physicochemical analysis of some specific IPN1 structures.
IPN1 moieties

| CM | pK | logD > pK | composite logo pH 4 | composite logD pH 7.4 | # C atoms for logD −1 | # C atoms for logD +3 |
|---|---|---|---|---|---|---|
| none | none | 0 | −4.3 | −3.9 | | |
| 1 | 8.28 | −1.21 | −5.41 | −7.51 | 8 | 16 |
| 4 | 8.97 | −1.08 | −5.28 | −7.38 | 8 | 16 |
| 5 | 8.08 | −0.59 | −4.79 | −6.89 | 7 | 15 |
| 15 | 9.9 | −0.33 | −4.53 | −6.63 | 7 | 15 |
| 21 | 11.26 | 0.37 | −3.83 | −5.93 | 5 | 13 |
| 22 | 10.03 | −0.23 | −4.43 | −6.53 | 6 | 14 |
| 23 pK1 | 10.33 | −1.23 | −5.43 | −7.53 | 8 | 16 |
| 24 | 10.9 | −1.08 | −5.28 | −7.38 | 8 | 16 |
| 25 | 9.7 | −0.72 | −4.92 | −7.02 | 7 | 15 |
| 31 | 8.97 | 0.93 | −3.27 | −5.37 | 4 | 12 |
| 32 pK1 | 9.9 | −1.17 | −5.37 | −7.47 | 8 | 16 |
| 33 | 10.87 | 1.38 | −2.82 | −4.92 | 3 | 11 |
| 49 | 9.79 | 0.49 | −3.71 | −5.81 | 5 | 13 |
| 50 | 8.93 | 0.16 | −4.04 | −6.14 | 6 | 14 |
| 51 pK1 | 9.57 | −0.64 | −4.84 | −6.94 | 7 | 15 |
| 52 | 9.74 | −1.95 | −6.15 | −8.25 | 10 | 18 |
| 53 | 8.47 | −1.58 | −5.78 | −7.88 | 9 | 17 |
| 56 | 9.04 | 1.06 | −3.14 | −5.24 | 4 | 12 |
| 57 pK1 | 9.27 | −0.45 | −4.65 | −6.75 | 7 | 15 |
| 64 pK1 | 8.69 | −1.93 | −6.13 | −8.23 | 10 | 18 |
| 72 | 8.41 | −1.52 | −5.72 | −7.82 | 9 | 17 |
| 73 | 8.33 | 0.36 | −3.84 | −5.94 | 5 | 13 |
| 82 pK1 | 8.35 | −0.79 | −4.99 | −7.09 | 7 | 15 |
| A1 | 10.66 | −0.68 | −4.88 | −6.98 | 7 | 15 |
| A2 | 10.73 | −0.45 | −4.65 | −6.75 | 7 | 15 |
| A3 | 9.75 | 0.06 | −4.14 | −6.24 | 6 | 14 |

TABLE 12-continued

Physicochemical analysis of some specific IPN1 structures.
IPN1 moieties

| CM | pK | logD > pK | composite logo pH 4 | composite logD pH 7.4 | # C atoms for logD −1 | # C atoms for logD +3 |
|---|---|---|---|---|---|---|
| A4 | 99 | 0.21 | −3.99 | −6.09 | 5 | 13 |
| A5 | 9.16 | −1.34 | −5.54 | −7.64 | 9 | 17 |
| A6 | 8.71 | −1.51 | −5.71 | −7.81 | 9 | 17 |
| A7 | 7.77 | −1.11 | −5.31 | −7.41 | 8 | 16 |
| A8 | 9.91 | −1.12 | −5.32 | −7.42 | 8 | 16 |
| A9 | 10.01 | −1.26 | −5.46 | −7.56 | 8 | 16 |
| A10 | 8.32 | −1.59 | −5.79 | −7.89 | 9 | 17 |
| A11 | 9.36 | −1.38 | −5.58 | −7.68 | 9 | 17 |
| A12 | 7.93 | −1.43 | −5.63 | −7.73 | 9 | 17 |
| A13 | 8.24 | −1.27 | −5.47 | −7.57 | 8 | 16 |
| AE5 | 7.55 | −0.82 | −5.02 | −7.12 | 8 | 16 |
| AE6 | 7.52 | 0.5 | −3.7 | −5.8 | 5 | 13 |
| AE17 | 7.8 | −0.23 | −4.43 | −6.53 | 6 | 14 |
| AE18 | 9.28 | −0.39 | −4.59 | −6.69 | 7 | 15 |
| AE37 | 8.71 | −1.52 | −5.72 | −7.82 | 9 | 17 |
| AE38 | 9.17 | −1.61 | −5.81 | −7.91 | 9 | 17 |
| AE43 | 8.6 | −2.75 | −6.95 | −9.05 | 11 | 19 |
| AE44 | 9.36 | −2.83 | −7.03 | −9.13 | 12 | 20 |
| AE46 | 8.67 | −1.44 | −5.64 | −7.74 | 9 | 17 |
| AE47 | 9.67 | −1.3 | −5.5 | −7.6 | 9 | 17 |
| AE48 | 7.87 | −0.99 | −5.19 | −7.29 | 8 | 16 |
| AE49 | 7.89 | −0.45 | −4.65 | −6.75 | 7 | 15 |
| AE50 pK1 | 13.37 | −2.15 | −6.35 | −8.45 | 10 | 18 |
| AE51 | 7.98 | 0.42 | −3.78 | −5.88 | 5 | 13 |
| AE52 | 7.95 | 0.42 | −3.78 | −5.88 | 5 | 13 |
| AE53 pK1 | 10.46 | −1.35 | −5.55 | −7.65 | 9 | 17 |
| AE55 | 7.92 | 0.61 | −3.59 | −5.69 | 5 | 13 |
| AE56 | 7.92 | 0.08 | −4.12 | −6.22 | 6 | 14 |
| AE57 pK1 | 10.14 | −1.27 | −5.47 | −7.57 | 8 | 16 |
| AE59 | 9.19 | −0.6 | −4.8 | −6.9 | 7 | 15 |
| AE60 | 7.8 | 0.69 | −3.51 | −5.61 | 5 | 13 |
| AE62 | 7.95 | −0.11 | −4.31 | −6.41 | 6 | 14 |
| AE65 pK1 | 9.67 | −1.65 | −5.85 | −7.95 | 9 | 17 |
| AE65 pK2 | 7.6 | −4.1 | −8.3 | −10.4 | 14 | 22 |
| AE66 pK1 | 9.51 | −1.57 | −5.77 | −7.87 | 9 | 17 |
| AE69 pK1 | 10.46 | −1.09 | −5.29 | −7.39 | 8 | 16 |
| AE70 pK1 | 10.14 | −1.01 | −5.21 | −7.31 | 8 | 16 |
| AE71 pK1 | 9.51 | −1.31 | −5.51 | −7.61 | 9 | 17 |
| AE72 pK1 | 9.67 | −1.38 | −5.58 | −7.68 | 9 | 17 |

To further illustrate, but not limit the teachings of this invention, the following table 13 presents some more specific chemical representations for IPN1 structures in nucleic acids, wherein Y is oxygen or sulphur, B represent any of the nucleobases or is absent, the index n denotes the length of the nucleic acid and n>2 and i denotes the length of an alkyl chain which here represents the hydrophobic moiety, (i−1) preferably falls within the range specified in table 12 for the respective compounds. More than one hydrophobic moiety can be used in the such cases the preferred range for their size indices k and j shall be selected to meet k+j=i−1.

From the IPN1 structures shown below it becomes clear that the attachment site of a given CM to the nucleoside sugar may vary and that some CM's can be inserted in different orientations. Also, the position of the hydrophobic element may vary and the position of the graft may be variable, as illustrated in the structures IPN1-10 through to IPN1-17.

TABLE 13

Specific representations of IPN1 structures.

IPN1-10

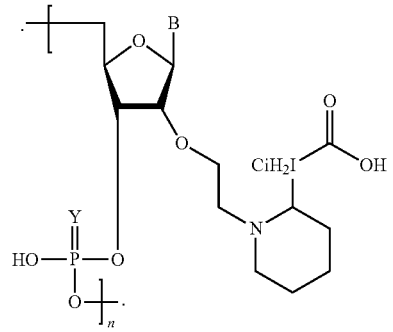

IPN1-11

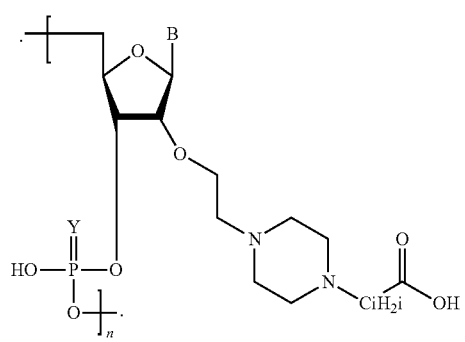

IPN1-12

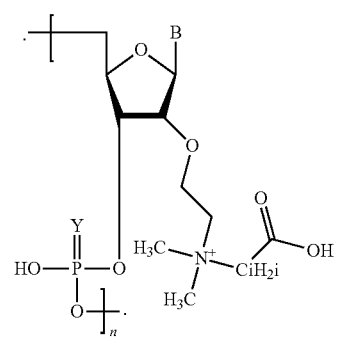

IPN1-13

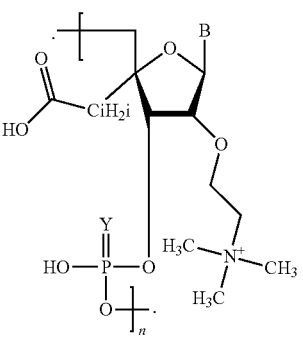

TABLE 13-continued

Specific representations of IPN1 structures.

IPN1-14

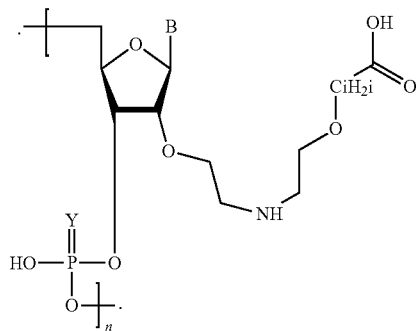

IPN1-15

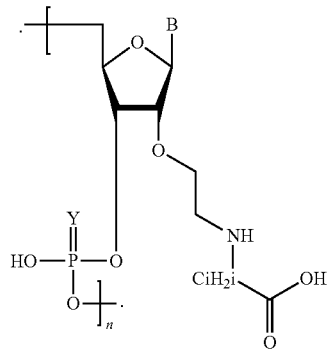

IPN1-16

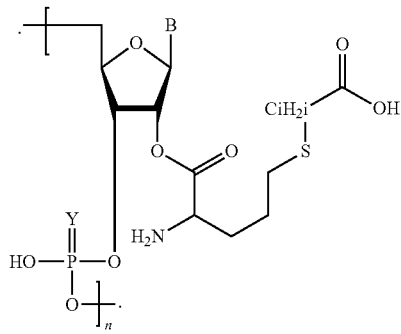

IPN1-17

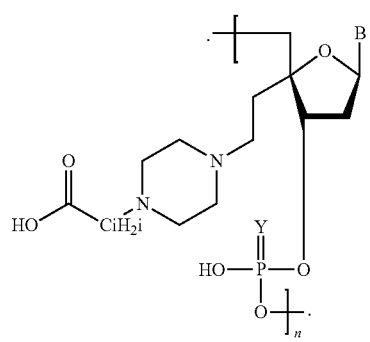

As disclosed above, the architecture of nucleic acids comprising IPN structures may vary and different degrees of substitution of native nucleic acids with IPN structures are possible. Also, such substitutions may be concentrated on specific sites within a nucleic acid, e.g. at one or both flanks of the sequence, at the center part of such sequence or they might be dispersed throughout the sequence. A known design in the art is a "gapmer", wherein modified sequences at the flanks of an oligonucleotide encompass an unmodified or differently modified sequence in a center piece.

The following table 14 gives calculated log D values for 20mer oligonucleotides having a degree of substitution of 50% and such log D values have been calculated for pH4 and pH7.4 and for different values of i, the length indicator for the hydrophobic element. For comparison, the log D (pH7.4) of an unmodified sequence of the same type is −81, that of pH4 is −89. The standard assumptions giving above for log D of the internucleoside linkage, nucleobases and zwitterionic interaction were used.

Introduction of IPN1 elements into an oligonucleotide, even at a limited degree of substitution leads to substantial improvements in log D and preferred oligonucleotides having a log D>−60 are highlighted in the table 14. Also, the IPN1 substitutions minimize or even reverse the pH-induced decrease of log D at low values of pH. In a third aspect, this analysis gives additional guidance on the number of carbon atoms i in the hydrophobic element that may be present in IPN1 structures. While i=12 yields preferred structures in almost any case, even the shorter element with i=8 is sufficient for most species analyzed here. Even more so, some species achieve substantial improvements in log D even with i=4.

TABLE 14 logD predictions for 20mers of oligonucleotides comprising 50% IPN1 structures. CM denotes structures as in table 2 herein.
20mer oligonucleotides, 50% substitution with IPN1

| CM | i = 4 | | i = 8 | | i = 12 | |
|---|---|---|---|---|---|---|
| | pH 4 | pH 7.4 | pH 4 | pH 7.4 | pH 4 | pH 7.4 |
| 1 | −80 | −97 | −60 | −77 | −40 | −57 |
| 4 | −79 | −96 | −59 | −76 | −39 | −56 |
| 5 | −74 | −91 | −54 | −71 | −34 | −51 |
| 15 | −71 | −88 | −51 | −68 | −31 | −48 |
| 21 | −64 | −81 | −44 | −61 | −24 | −41 |
| 22 | −70 | −87 | −50 | −67 | −30 | −47 |
| 23 pK1 | −80 | −97 | −60 | −77 | −40 | −57 |
| 24 | −79 | −96 | −59 | −76 | −39 | −56 |
| 25 | −75 | −92 | −55 | −72 | −35 | −52 |
| 31 | −59 | −76 | −39 | −56 | −19 | −36 |
| 32 pK1 | −80 | −97 | −60 | −77 | −40 | −57 |
| 33 | −54 | −71 | −34 | −51 | −14 | −31 |
| 49 | −63 | −80 | −43 | −60 | −23 | −40 |
| 50 | −66 | −83 | −46 | −63 | −26 | −43 |
| 51 pK1 | −74 | −91 | −54 | −71 | −34 | −51 |
| 52 | −88 | −105 | −68 | −85 | −48 | −65 |
| 53 | −84 | −101 | −64 | −81 | −44 | −61 |
| 56 | −57 | −74 | −37 | −54 | −17 | −34 |
| 57 pK1 | −73 | −90 | −53 | −70 | −33 | −50 |
| 64 pK1 | −87 | −104 | −67 | −84 | −47 | −64 |
| 72 | −83 | −100 | −63 | −80 | −43 | −60 |
| 73 | −64 | −81 | −44 | −61 | −24 | −41 |
| 82 pK1 | −76 | −93 | −56 | −73 | −36 | −53 |
| A1 | −75 | −92 | −55 | −72 | −35 | −52 |
| A2 | −73 | −90 | −53 | −70 | −33 | −50 |
| A3 | −67 | −84 | −47 | −64 | −27 | −44 |
| A4 | −66 | −83 | −46 | −63 | −26 | −43 |
| A5 | −81 | −98 | −61 | −78 | −41 | −58 |
| A6 | −83 | −100 | −63 | −80 | −43 | −60 |
| A7 | −79 | −96 | −59 | −76 | −39 | −56 |
| A8 | −79 | −96 | −59 | −76 | −39 | −56 |

TABLE 14-continued logD predictions for 20mers of oligonucleotides comprising 50% IPN1 structures. CM denotes structures as in table 2 herein.
20mer oligonucleotides, 50% substitution with IPN1

| | i = 4 | | i = 8 | | i = 12 | |
|---|---|---|---|---|---|---|
| CM | pH 4 | pH 7.4 | pH 4 | pH 7.4 | pH 4 | pH 7.4 |
| A9 | −81 | −98 | −61 | −78 | −41 | −58 |
| A10 | −84 | −101 | −64 | −81 | −44 | −61 |
| A11 | −82 | −99 | −62 | −79 | −42 | −59 |
| A12 | −82 | −99 | −62 | −79 | −42 | −59 |
| A13 | −81 | −98 | −61 | −78 | −41 | −58 |
| AE5 | −76 | −93 | −56 | −73 | −36 | −53 |
| AE6 | −63 | −80 | −43 | −60 | −23 | −40 |
| AE17 | −70 | −87 | −50 | −67 | −30 | −47 |
| AE18 | −72 | −89 | −52 | −69 | −32 | −49 |
| AE37 | −83 | −100 | −63 | −80 | −43 | −60 |
| AE38 | −84 | −101 | −64 | −81 | −44 | −61 |
| AE43 | −96 | −113 | −76 | −93 | −56 | −73 |
| AE44 | −96 | −113 | −76 | −93 | −56 | −73 |
| AE46 | −82 | −99 | −62 | −79 | −42 | −59 |
| AE47 | −81 | −98 | −61 | −78 | −41 | −58 |
| AE48 | −78 | −95 | −58 | −75 | −38 | −55 |
| AE49 | −73 | −90 | −53 | −70 | −33 | −50 |
| AE50 pK1 | −90 | −107 | −70 | −87 | −50 | −67 |
| AE51 | −64 | −81 | −44 | −61 | −24 | −41 |
| AE52 | −64 | −81 | −44 | −61 | −24 | −41 |
| AE53 pK1 | −82 | −99 | −62 | −79 | −42 | −59 |
| AE55 | −62 | −79 | −42 | −59 | −22 | −39 |
| AE56 | −67 | −84 | −47 | −64 | −27 | −44 |
| AE57 pK1 | −81 | −98 | −61 | −78 | −41 | −58 |
| AE59 | −74 | −91 | −54 | −71 | −34 | −51 |
| AE60 | −61 | −78 | −41 | −58 | −21 | −38 |
| AE62 | −69 | −86 | −49 | −66 | −29 | −46 |
| AE65 pK1 | −85 | −102 | −65 | −82 | −45 | −62 |
| AE65 pK2 | −109 | −126 | −89 | −106 | −69 | −86 |
| AE66 pK1 | −84 | −101 | −64 | −81 | −44 | −61 |
| AE69 pK1 | −79 | −96 | −59 | −76 | −39 | −56 |
| AE70 pK1 | −78 | −95 | −58 | −75 | −38 | −55 |
| AE71 pK1 | −81 | −98 | −61 | −78 | −41 | −58 |
| AE72 pK1 | −82 | −99 | −62 | −79 | −42 | −59 |

IPN3 Structures.

The description given so far is also sufficient to construct complete nucleic acid monomer units as IPN3 structures. The preferred internucleoside linkage is of phosphodiester, phosphothioate, or phosphodithioate type, but other linkages can be used as long as they provide a negative charge. IPN3 structures comprise a CM that responds to pH between pH4 and pH7.4, and in preferred embodiments of IPN3, the pK of the CM is between 4 and 7.5, more preferred is a pK between 5 and 6.5. Besides their CM, IPN3 structures further comprise a TEE.

The core architecture of some IPN3 nucleic acid monomers is presented in table 15.

TABLE 15

Core structures of IPN3 elements (IPN3-1)

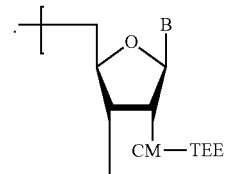

(IPN3-2)

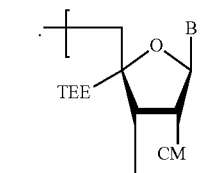

(IPN3-3)

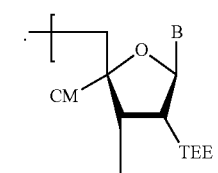

(IPN3-4)

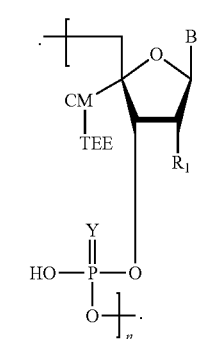

TABLE 15-continued

Core structures of IPN3 elements (IPN3-5)

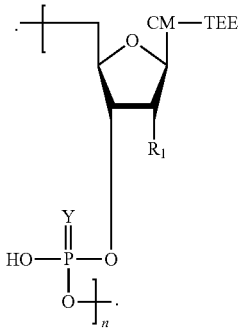

(IPN3-6)

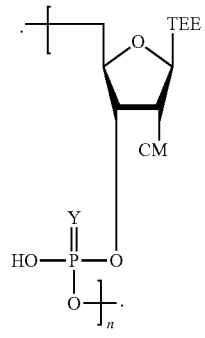

In many aspects of the inventive IPN3 structures, the weak acid of the TEE is a carboxylic acid.

In preferred embodiments of IPN3 structures, the hydrophobic element of the TEE is directly attached to the CM as in IPN3-1, IPN3-4 or IPN3-5.

In most aspects, the log D(pH4) of an IPN3 nucleotide is higher than −2, in preferred aspects this value is between −1 and +3 and in some aspects it is greater than 3. Said log D refers to the chain form for the IPN3 nucleotide and represents the monomer increment per nucleotide, it is different from the IPN3 monomer itself mainly due to the presence of the second charge at the phosphate group.

The log D of IPN3 structures can be considered as a composite from (i) the backbone elements internucleoside linkage and nucleoside sugar, (ii) the nucleobases itself, if present, (iii) the CM and (iv) the pH dependent zwitterion formation between CM and internucleoside linkage and (v) the TEE. Quantitative estimates for the composite elements have been presented above and approximate values for (i) are −2 to −3; (ii) is pH dependent and about −1.4 at pH 7.4 and −1.8 at pH4; values for (iii) are listed in tables 3 to 5 for the unprotonated form at pH>pK and (iv) is about +1 for the zwitterion formation. For (v), the contribution of the TEE can be segmented into the contribution of the hydrophilic moiety and the hydrophobic moiety to simplify the assignment of the number of elements in the hydrophobic moiety. Data provided in PCT/EP2007/011188 for the relationship between the number of methylene groups in carboxylic acids and the resulting log D values can be extrapolated to conclude the contributions of this charged element. The resulting values are −0.9 for the uncharged and −3.4 for the charged state of this element. The TEE also comprises a hydrophobic element, since without such element the net contribution of the charged group to the log D is negative. For practicing this invention, the global log D of the IPN structure is of importance, it is less important whether the CM and its hydrophobic additions or the TEE and its hydrophobic element contribute the required hydrophobicity. In many embodiments of the IPN3 and IPN3 structures this hydrophobic moiety can be common structure of the CM and the TEE.

The following table 16 presents specific composite log D for some of the IPN3 structures comprising any of the core unit of IPN3-1 through to IPN3-4 using the data presented in the tables 3 to 5 above. It is of course possible to analyze structures of different chemical origin in the same way; this analysis is illustrating, but not limiting the teachings of this invention. The composite log D values do comprise the elements (i) to (v) presented before for IPN3 structures and are given for both the neutral pH and an acidic pH; these composite log D's are extrapolated for species wherein the hydrophobic moiety of the TEE is absent. This allows identifying preferred ranges for the size of said hydrophobic elements and said ranges are given in the last two columns of this table 16 for cases where the hydrophobic elements are methylene groups. Preferred hydrophobic moieties comprise between 4 and 22 carbon atoms. REF1 teaches that the specific chemical configuration of such hydrophobic moieties has little impact on the log D contribution; REF1 has also analyzed the impact of potential substitutions to such hydrophobic moieties. In many cases the specific position of the hydrophobic moiety on the core structures (IPN3-1)-(IPN3-4) may also vary without substantial impact to the physicochemical parameters.

TABLE 16

Physicochemical analysis of some specific IPN3 structures.
CM denotes the structures listed in table 2 herein.

IPN3 moieties

| CM | pK | logD > pK | composite logD pH 4 | composite logD pH 7.4 | # C atoms for logD −1 | # C atoms for logD +3 |
|---|---|---|---|---|---|---|
| none | none | 0 | −4.3 | −3.9 | | |
| 3 | 5.56 | −1.92 | −6.12 | −9.22 | 10 | 18 |
| 6 | 5.08 | −0.95 | −5.15 | −8.25 | 8 | 16 |
| 7 | 5.5 | −0.39 | −4.59 | −7.69 | 7 | 15 |
| 10 | 5.45 | 0.18 | −4.02 | −7.12 | 6 | 14 |
| 13 | 7 | −1.49 | −5.69 | −8.79 | 9 | 17 |
| 16 | 6.54 | −1.86 | −6.06 | −9.16 | 10 | 18 |
| 27 | 5.23 | 0.73 | −3.47 | −6.57 | 4 | 12 |
| 32 pK2 | 5.3 | −4.1 | −8.3 | −11.4 | 14 | 22 |
| 40 | 6.58 | −0.74 | −4.94 | −8.04 | 7 | 15 |
| 41 | 6.95 | −0.6 | −4.8 | −7.9 | 7 | 15 |
| 42 | 6.58 | 0.55 | −3.65 | −6.75 | 5 | 13 |
| 46 | 5.94 | −1.02 | −5.22 | −8.32 | 8 | 16 |
| 47 | 5.31 | −2.55 | −6.75 | −9.85 | 11 | 19 |
| 48 | 6.78 | −0.63 | −4.83 | −7.93 | 7 | 15 |
| 54 | 6.13 | −1.3 | −5.5 | −8.6 | 9 | 17 |
| 55 | 5.01 | −0.46 | −4.66 | −7.76 | 7 | 15 |
| 60 | 5.16 | −1.21 | −5.41 | −8.51 | 8 | 16 |
| 63 | 5.34 | −1.9 | −6.1 | −9.2 | 10 | 18 |
| 66 | 5.31 | −0.39 | −4.59 | −7.69 | 7 | 15 |
| 69 | 6.21 | −0.61 | −4.81 | −7.91 | 7 | 15 |
| 70 | 5.53 | −0.9 | −5.1 | −8.2 | 8 | 16 |
| 71 | 6.6 | 0.39 | −3.81 | −6.91 | 5 | 13 |
| 74 | 6.44 | −1.36 | −5.56 | −8.66 | 9 | 17 |
| 81 pK2 | 5.51 | −4.5 | −8.7 | −11.8 | 15 | 23 |
| 82 pK2 | 6.48 | −3.8 | −8 | −11.1 | 14 | 22 |
| AE1 | 6.39 | −1.26 | −5.46 | −8.56 | 8 | 16 |
| AE2 | 6.21 | −0.38 | −4.58 | −7.68 | 7 | 15 |
| AE7 | 6.2 | −2.07 | −6.27 | −9.37 | 10 | 18 |
| AE8 | 6.14 | −0.77 | −4.97 | −8.07 | 7 | 15 |
| AE9 | 6.51 | −1.18 | −5.38 | −8.48 | 8 | 16 |

TABLE 16-continued

Physicochemical analysis of some specific IPN3 structures.
CM denotes the structures listed in table 2 herein.
IPN3 moieties

| CM | pK | logD > pK | composite logD pH 4 | composite logD pH 7.4 | # C atoms for logD −1 | # C atoms for logD +3 |
|---|---|---|---|---|---|---|
| AE10 | 6.6 | −0.55 | −4.75 | −7.85 | 7 | 15 |
| AE11 | 6.75 | −1.61 | −5.81 | −8.91 | 9 | 17 |
| AE12 | 6.79 | −0.24 | −4.44 | −7.54 | 6 | 14 |
| AE14 | 5.9 | −0.65 | −4.85 | −7.95 | 7 | 15 |
| AE15 | 6.9 | −0.541 | −4.741 | −7.841 | 7 | 15 |
| AE16 | 6.75 | −0.32 | −4.52 | −7.62 | 7 | 15 |
| AE21 | 6.3 | −2.1 | −6.3 | −9.4 | 10 | 18 |
| AE22 | 6.11 | −0.58 | −4.78 | −7.88 | 7 | 15 |
| AE24 | 6.95 | −0.59 | −4.79 | −7.89 | 7 | 15 |
| AE27 | 5.18 | −2.75 | −6.95 | −10.05 | 11 | 19 |
| AE28 | 5.75 | −1.46 | −5.66 | −8.76 | 9 | 17 |
| AE29 | 6.12 | −1.86 | −6.06 | −9.16 | 10 | 18 |
| AE30 | 6.22 | −1.23 | −5.43 | −8.53 | 8 | 16 |
| AE31 | 6.36 | −2.3 | −6.5 | −9.6 | 11 | 19 |
| AE32 | 6.4 | −0.92 | −5.12 | −8.22 | 8 | 16 |
| AE34 | 5.8 | −1.36 | −5.56 | −8.66 | 9 | 17 |
| AE35 | 6.8 | −1.46 | −5.66 | −8.76 | 9 | 17 |
| AE36 | 6.52 | −1.51 | −5.71 | −8.81 | 9 | 17 |
| AE40 | 5.58 | −2.59 | −6.79 | −9.89 | 11 | 19 |
| AE41 | 6.68 | −2.68 | −6.88 | −9.98 | 11 | 19 |
| AE42 | 6.29 | −2.73 | −6.93 | −10.03 | 11 | 19 |
| AE54 | 6.96 | 0.07 | −4.13 | −7.23 | 6 | 14 |
| AE57 pK2 | 6.87 | −3.8 | −8 | −11.1 | 14 | 22 |
| AE63 | 6.41 | −0.72 | −4.92 | −8.02 | 7 | 15 |
| AE64 | 6.41 | −1.06 | −5.26 | −8.36 | 8 | 16 |
| AE67 | 5.99 | 0.33 | −3.87 | −6.97 | 5 | 13 |
| AE68 | 6.02 | 0.94 | −3.26 | −6.36 | 4 | 12 |
| AE69 pK2 | 6.17 | −3.8 | −8 | −11.1 | 14 | 22 |
| AE70 pK2 | 5.72 | −3.66 | −7.86 | −10.96 | 13 | 21 |
| AE71 pK2 | 6.09 | −4 | −8.2 | −11.3 | 14 | 22 |
| AE72 pK2 | 6.32 | −3.9 | −8.1 | −11.2 | 14 | 22 |

To further illustrate, but not limit the teachings of this invention, the following table 17 presents some more specific chemical representations for IPN3 structures in nucleic acids, wherein Y is oxygen or sulphur, B represent any of the nucleobases or is absent, the index n denotes the length of the nucleic acid and n>2 and i denotes the length of an alkyl chain which here represents the hydrophobic moiety, (i−1) preferably falls within the range specified in table 16 for the respective compounds. More than one hydrophobic moiety can be used in the such cases the preferred range for their size indices k and j shall be selected to meet k+j=i−1.

From the IPN3 structures shown below it becomes clear that the attachment site of a given CM to the nucleoside sugar may vary and that some CM's can be inserted in different orientations. Also, the position of the hydrophobic element may vary and the position of the graft may be variable, as illustrated in the structures IPN3-10 through to IPN3-21.

TABLE 17

Specific representations of IPN3 structures.

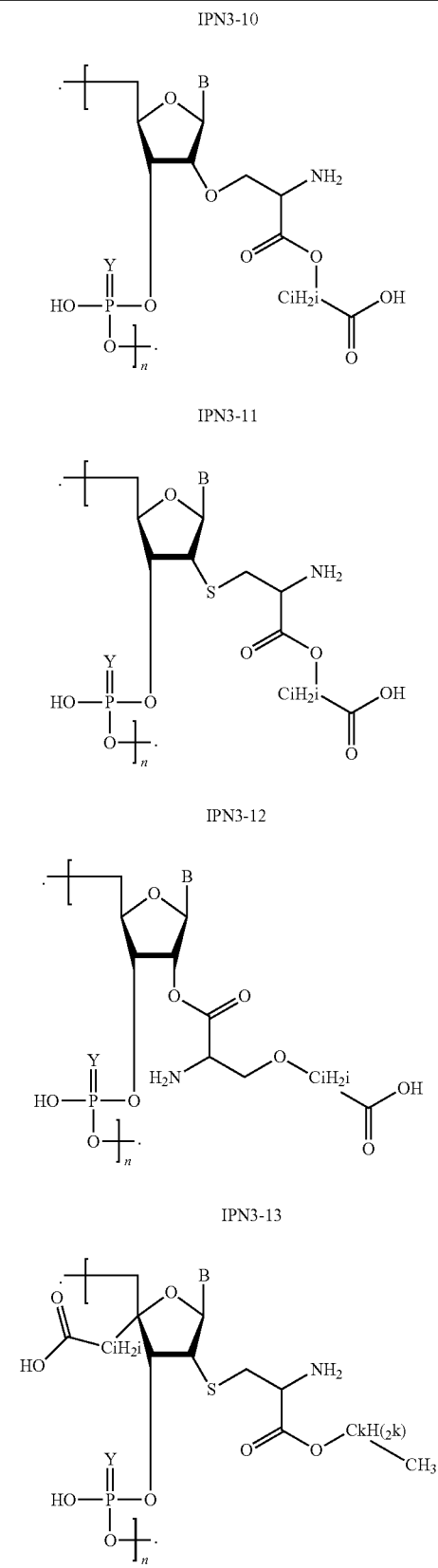

TABLE 17-continued
Specific representations of IPN3 structures.
IPN3-14
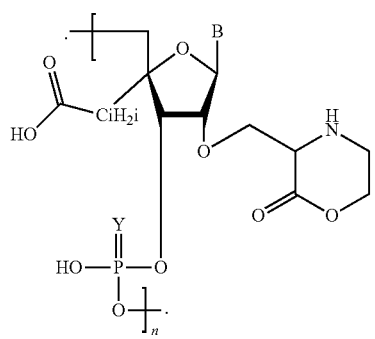
IPN3-15
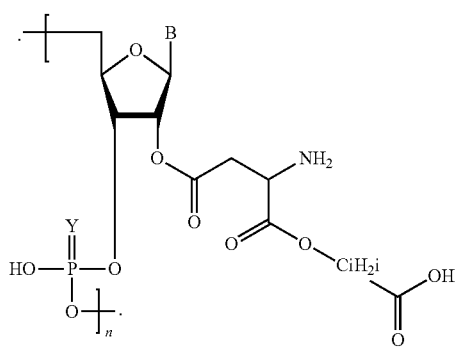
IPN3-16
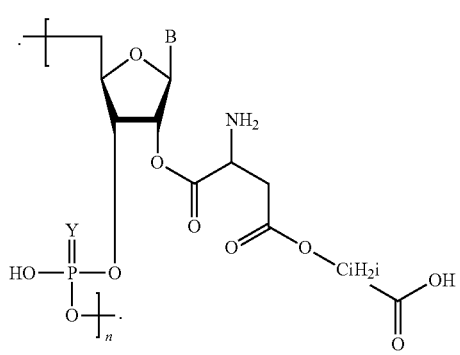
IPN3-17
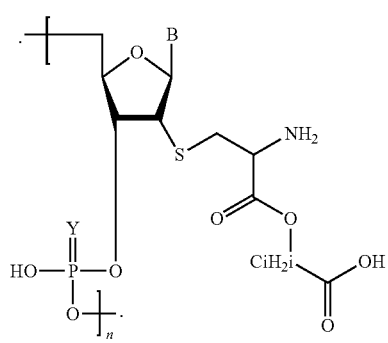
TABLE 17-continued
Specific representations of IPN3 structures.
IPN3-18
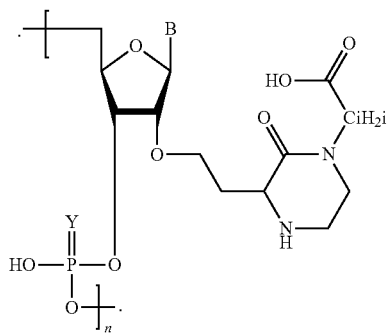
IPN3-19
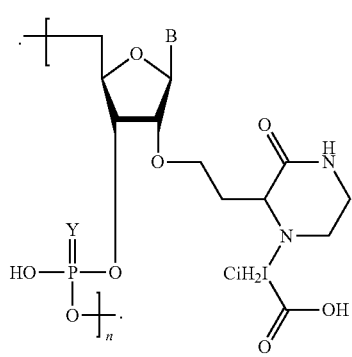
IPN3-20
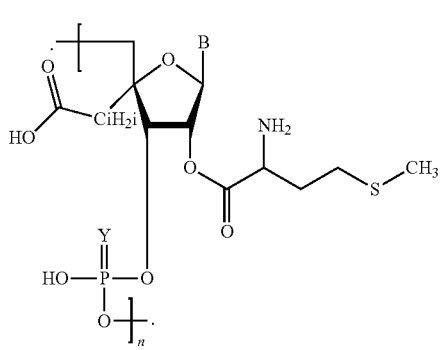
IPN3-21
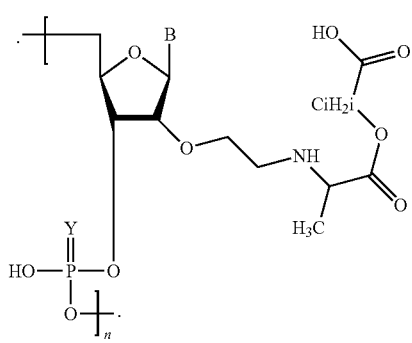

TABLE 17-continued

Specific representations of IPN3 structures.

IPN3-22

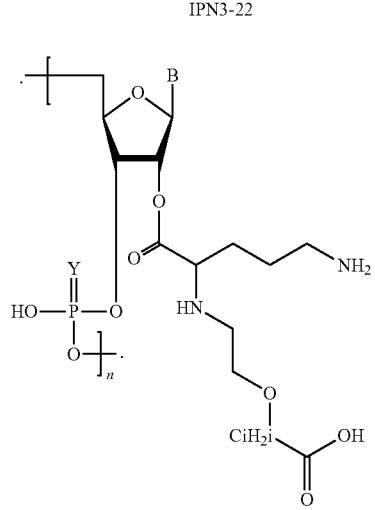

IPN3-23

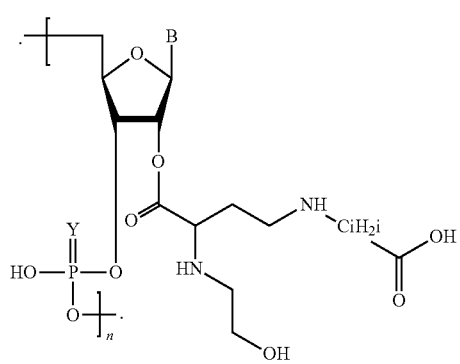

IPN3-24

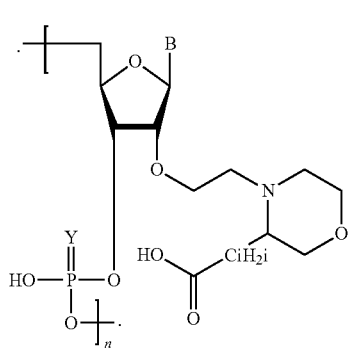

TABLE 17-continued

Specific representations of IPN3 structures.

IPN3-25

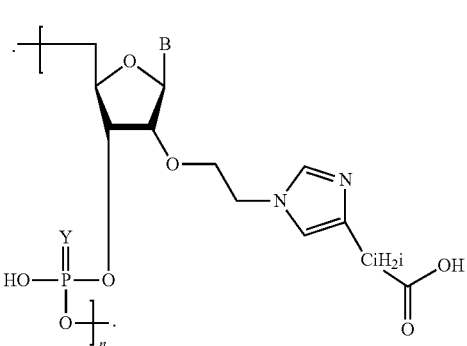

IPN3-26

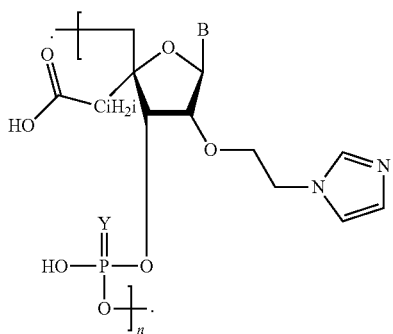

IPN3-27

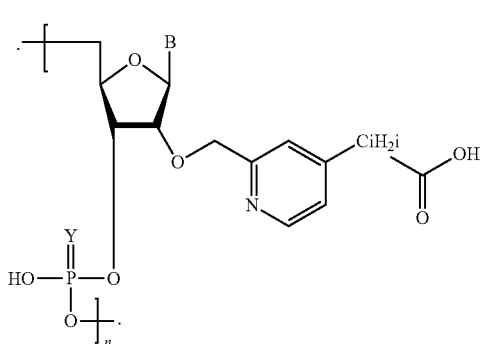

As disclosed above, the architecture of nucleic acids comprising IPN structures may vary and different degrees of substitution of native nucleic acids with IPN structures are possible. Also, such substitutions may be concentrated on specific sites within a nucleic acid, e.g. at one or both flanks of the sequence, at the center part of such sequence or they might be dispersed throughout the sequence. A known design in the art is a "gapmer", wherein modified sequences at the flanks of an oligonucleotide encompass an unmodified or differently modified sequence in a center piece.

The following table 18 gives calculated log D values for 20mer oligonucleotides having a degree of substitution of 50% and such log D values have been calculated for pH4 and pH7.4 and for different values of i, the length indicator for the hydrophobic element. For comparison, the log D (pH7.4) of an unmodified sequence of the same type is −81, that of pH4 is −89. The standard assumptions giving above for log D of the internucleoside linkage, nucleobases and zwitterionic interaction were used.

Introduction of IPN3 elements into an oligonucleotide, even at a limited degree of substitution leads to substantial improvements in log D and preferred oligonucleotides having a log D>−60 are highlighted in the table 18. Also, the IPN3 substitutions minimize or even reverse the pH-induced decrease of log D at low values of pH. In a third aspect, this analysis gives additional guidance on the number of carbon atoms (i) in the hydrophobic element that may be present in IPN3 structures. While i=12 yields preferred structures in almost any case, even the short element with i=8 is sufficient for most species analyzed here. Even more so, some species achieve substantial improvements in log D even with i=4.

TABLE 18 logD predictions for 20mers of oligonucleotides comprising 50% IPN3 structures. CM denotes the structures from table 2 herein.
20mer oligonucleotides, 50% substitution with IPN3

| CM | i = 4 | | i = 8 | | i = 12 | |
|---|---|---|---|---|---|---|
| none | pH 4 | pH 7.4 | pH 4 | pH 7.4 | pH 4 | pH 7.4 |
| 3 | −87 | −114 | −67 | −94 | −47 | −74 |
| 6 | −78 | −105 | −58 | −85 | −38 | −65 |
| 7 | −72 | −99 | −52 | −79 | −32 | −59 |
| 10 | −66 | −93 | −46 | −73 | −26 | −53 |
| 13 | −83 | −110 | −63 | −90 | −43 | −70 |
| 16 | −87 | −114 | −67 | −94 | −47 | −74 |
| 27 | −61 | −88 | −41 | −68 | −21 | −48 |
| 32 pK2 | −109 | −136 | −89 | −116 | −69 | −96 |
| 40 | −75 | −102 | −55 | −82 | −35 | −62 |
| 41 | −74 | −101 | −54 | −81 | −34 | −61 |
| 42 | −63 | −90 | −43 | −70 | −23 | −50 |
| 46 | −78 | −105 | −58 | −85 | −38 | −65 |
| 47 | −94 | −121 | −74 | −101 | −54 | −81 |
| 48 | −74 | −101 | −54 | −81 | −34 | −61 |
| 54 | −81 | −108 | −61 | −88 | −41 | −68 |
| 55 | −73 | −100 | −53 | −80 | −33 | −60 |
| 60 | −80 | −107 | −60 | −87 | −40 | −67 |
| 63 | −87 | −114 | −67 | −94 | −47 | −74 |
| 66 | −72 | −99 | −52 | −79 | −32 | −59 |
| 69 | −74 | −101 | −54 | −81 | −34 | −61 |
| 70 | −77 | −104 | −57 | −84 | −37 | −64 |
| 71 | −64 | −91 | −44 | −71 | −24 | −51 |
| 74 | −82 | −109 | −62 | −89 | −42 | −69 |
| 81 pK2 | −113 | −140 | −93 | −120 | −73 | −100 |
| 82 pK2 | −106 | −133 | −86 | −113 | −66 | −93 |
| AE1 | −81 | −108 | −61 | −88 | −41 | −68 |
| AE2 | −72 | −99 | −52 | −79 | −32 | −59 |
| AE7 | −89 | −116 | −69 | −96 | −49 | −76 |
| AE8 | −76 | −103 | −56 | −83 | −36 | −63 |
| AE9 | −80 | −107 | −60 | −87 | −40 | −67 |
| AE10 | −74 | −101 | −54 | −81 | −34 | −61 |
| AE11 | −84 | −111 | −64 | −91 | −44 | −71 |
| AE12 | −70 | −97 | −50 | −77 | −30 | −57 |
| AE14 | −75 | −102 | −55 | −82 | −35 | −62 |
| AE15 | −73 | −100 | −53 | −80 | −33 | −60 |
| AE16 | −71 | −98 | −51 | −78 | −31 | −58 |
| AE21 | −89 | −116 | −69 | −96 | −49 | −76 |
| AE22 | −74 | −101 | −54 | −81 | −34 | −61 |
| AE24 | −74 | −101 | −54 | −81 | −34 | −61 |

TABLE 18-continued logD predictions for 20mers of oligonucleotides comprising 50% IPN3 structures. CM denotes the structures from table 2 herein.
20mer oligonucleotides, 50% substitution with IPN3

| CM | i = 4 | | i = 8 | | i = 12 | |
|---|---|---|---|---|---|---|
| none | pH 4 | pH 7.4 | pH 4 | pH 7.4 | pH 4 | pH 7.4 |
| AE27 | −96 | −123 | −76 | −103 | −56 | −83 |
| AE28 | −83 | −110 | −63 | −90 | −43 | −70 |
| AE29 | −87 | −114 | −67 | −94 | −47 | −74 |
| AE30 | −80 | −107 | −60 | −87 | −40 | −67 |
| AE31 | −91 | −118 | −71 | −98 | −51 | −78 |
| AE32 | −77 | −104 | −57 | −84 | −37 | −64 |
| AE34 | −82 | −109 | −62 | −89 | −42 | −69 |
| AE35 | −83 | −110 | −63 | −90 | −43 | −70 |
| AE36 | −83 | −110 | −63 | −90 | −43 | −70 |
| AE40 | −94 | −121 | −74 | −101 | −54 | −81 |
| AE41 | −95 | −122 | −75 | −102 | −55 | −82 |
| AE42 | −95 | −122 | −75 | −102 | −55 | −82 |
| AE54 | −67 | −94 | −47 | −74 | −27 | −54 |
| AE57 pK2 | −106 | −133 | −86 | −113 | −66 | −93 |
| AE63 | −75 | −102 | −55 | −82 | −35 | −62 |
| AE64 | −79 | −106 | −59 | −86 | −39 | −66 |
| AE67 | −65 | −92 | −45 | −72 | −25 | −52 |
| AE68 | −59 | −86 | −39 | −66 | −19 | −46 |
| AE69 pK2 | −106 | −133 | −86 | −113 | −66 | −93 |
| AE70 pK2 | −105 | −132 | −85 | −112 | −65 | −92 |
| AE71 pK2 | −108 | −135 | −88 | −115 | −68 | −95 |
| AE72 pK2 | −107 | −134 | −87 | −114 | −67 | −94 |

The teachings of this invention have been demonstrated using phosphoribose as a backbone structure of the nucleic acids; however, the biophysical principles used herein can of course be applied to other and related structures. It is possible to replace the ribose ring in the nucleosides by other furanoses, by pyranoses or by hexitol ring structures. Also, the use of locked nucleic acids, that is nucleic acids comprising a 2', 4' methoxy or ethoxy bridge or the use of open structures that are devoid of the oxygen in the furanose ring (so called unlocked nucleic acids) is well within the teachings of this invention.

It is also possible to further substitute the backbone structure with hydroxyl or alkoxy groups so that hemiacetals or acetals are formed. According to REF1, any additional hydroxyl group is expected to further decrease the log D of a given structure by about 2 units. In contrast, only very small changes of log D or even an increase of its value were observed when calculating this parameter for hemiacetals or acetals of furanose or pyranose ring structures. In consequence, shorter hydrophobic elements are needed and the number of C atoms in these can be reduced. The tables 19 and 20 illustrate this part of the invention without limiting its scope.

TABLE 19
Alternative nucleoside structures having hemiacetal or acetal structures. n >= 2, B is any nucleobase selected from adenine, guanine, thymine, cytosine or uracile; Y is oxygen or sulphur, the CM of this example is AE1 and can be substituted by the other CM's mentioned throughout this invention.
N1
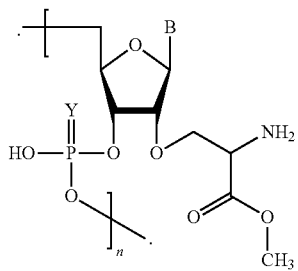
N2
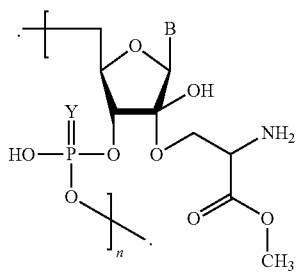
N3
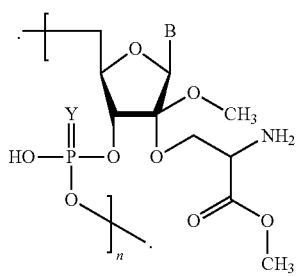
N4
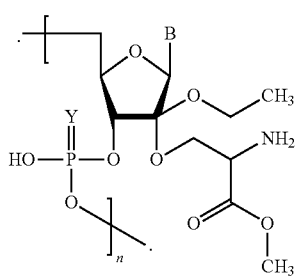

TABLE 19-continued
Alternative nucleoside structures having hemiacetal or acetal structures. n >= 2, B is any nucleobase selected from adenine, guanine, thymine, cytosine or uracile; Y is oxygen or sulphur, the CM of this example is AE1 and can be substituted by the other CM's mentioned throughout this invention.
N5
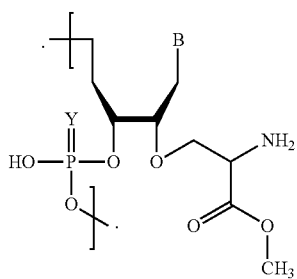
N6
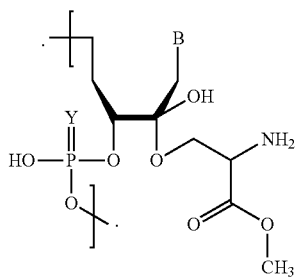
N7
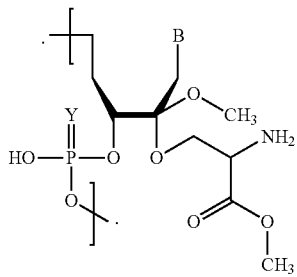
N8
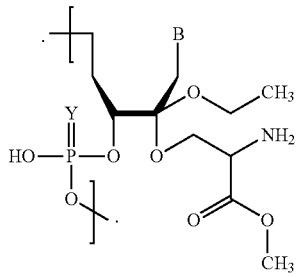

TABLE 20

Analysis of logD contribution for the structures listed in table 19. The relative logD listed herein compares the actual logD to that of the ribose form. Actual logD values for a specific hemiacetals or acetals can be calculated by adding this value to the logD value of the respective ribose form from the tables shown earlier in this disclosure, in particular tables 8, 12 and 16. The "relative number of C atoms" follow the same logic.

| Structure | Relative logD | Relative number of C atoms |
|---|---|---|
| N1 | 0 (unsubstituted ribose, reference structure) | 0 (unsubstituted ribose, reference structure) |
| N2 | +0.67 | −1 |
| N3 | +0.89 | −2 |
| N4 | +1.42 | −3 |
| N5 | +1.18 | −2 |
| N6 | +1.76 | −3 |
| N7 | +2.57 | −5 |
| N8 | +3.1 | −6 |

It is therefore possible to use the hemiacetals or acetals of arabinoside nucleosides as shown in the prototype structures N1-N4 or those of the unlocked nucleic acids as illustrated with the prototype structures N5-N8.

From the description made throughout this disclosure it becomes clear that the beneficial effects of the cationic moiety forming the zwitterionic structure, the TEE undergoing a pH driven hydrophobic transition and the general increase of hydrophobicity contributed by the hydrophobic moieties are by and large additive. This allows mesoscale predictions of log D values for larger structures such as oligonucleotides that cannot easily be predicted on their atomistic level. It also facilitates an analysis of oligonucleotides carrying mixed nucleotides, such as native and IPN modified nucleotides. The additive effect of said substitutions can also be used to design nucleic acids carrying different backbone modifications. At the end, much more detailed predictions for specific sequences and modification patterns can be achieved using the mesoscale approach presented herein and such predictions are well within the teachings of this invention.

The additive effect of the modifications to the nucleic acids also supports the construction of nucleic acids wherein mixed modifications of IPN's and the TEE-modified nucleotides of the REF1 are used.

The IPN of this invention or the TEE modified oligonucleotides of REF1 both represent nucleotide structures that undergo a hydrophilic-hydrophobic transition when exposed to a slightly acidic environment. Depending on the type of modification, the pH induced amplitude in log D may vary and typical values for such amplitude are about +1 per abasic IPN2 monomer, +2.5 per abasic IPN1 monomer or per TEE modified nucleotide of REF1 or +3.5 per abasic IPN3 monomer. As such, quite substantial changes in the hydrophobic character of a nucleotide can be induced by the inventive structures. As one consequence, the additional need for hydrophobic elements has been shown to be rather moderate, with i=4 to 12 methylene groups yielding significant improvements in the cellular permeability of larger nucleic acids even at a limited degree of substitution.

DESCRIPTION OF THE FIGURES

FIG. 1: pH dependent log D values for IPN structures. Log D values for compounds (CM4), (CM5), (CM6) and (CM7) have been analyzed over a range of different pH values. Calculations were done using the log D module of the ACD/Labs 7.00 software package. For comparison with structures not comprising a CM, the respective values for a methylated 3' phosphoribose are presented.

What is claimed is:

1. Nucleic acid comprising pH-responsive zwitterionic nucleotides of the following formula:

wherein
B is a nucleobase selected from adenine, guanine, thymine, cytosine or uracil;
Y is oxygen or sulphur;
n (number of nucleotides) is $>=2$;
CM is a cationic moiety which is a nitrogen base having a pK equal to or greater than 7.5 or a constantly charged cationic moiety comprising an ammonium or guanidinium group; and
TEE stands for a transfection enhancer element having the general formula (I):

Hydrophobic element-pH-responsive hydrophilic elements (I), wherein said hydrophobic element is a linear, branched or cyclic chain comprising 6 to 40 carbon atoms in the form of hydrocarbons or methylene groups, and said pH-responsive hydrophilic element is a carboxylic acid.

2. The nucleic acid according to claim 1, wherein said hydrophobic element of said TEE comprises more than 6 and up to 40 carbon atoms.

3. The nucleic acid according to claim 1, wherein said hydrophobic element of said TEE comprises from 6 to 22 carbon atoms.

4. The nucleic acid according to claim 1, wherein said hydrophobic element is a hydrocarbon group.

5. The nucleic acid according to claim 1, wherein said hydrophobic element consists of methylene groups.

6. The nucleic acid according to claim 1, wherein said nucleotides are selected from the following structures wherein $C_iH_{2i}$ is a hydrocarbon chain having the length i:

IPN1-10

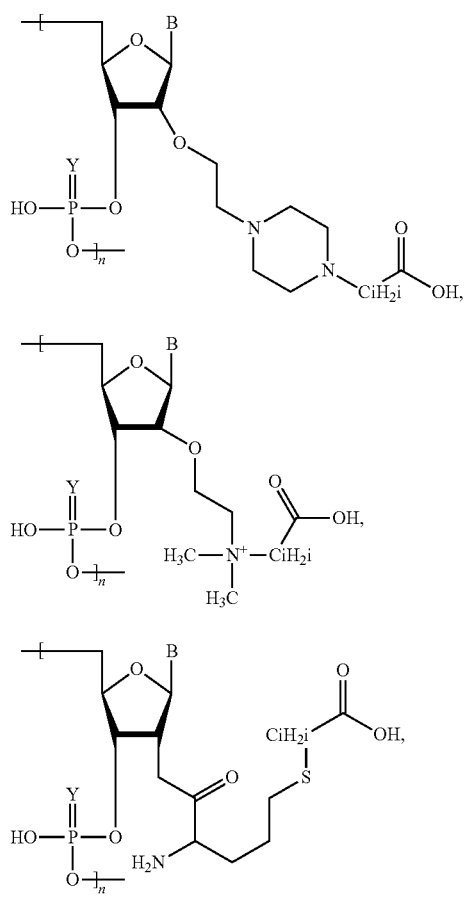
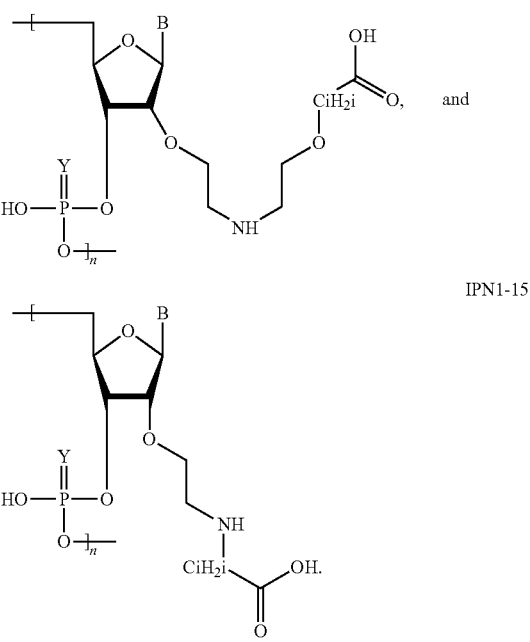
7. The nucleic acid according to claim 1, wherein said hydrophobic element of said TEE is directly attached to moiety CM.
8. The nucleic acid according to claim 1, wherein no more than ⅔ of all nucleotides in said nucleic acid are of IPN type.
9. The nucleic acid according to claim 1, wherein about 50% of all nucleotides in said nucleic acid are of IPN type.
* * * * *